(12) United States Patent
Gupta et al.

(10) Patent No.: US 10,029,047 B2
(45) Date of Patent: *Jul. 24, 2018

(54) PATIENT-SPECIFIC MEDICATION MANAGEMENT SYSTEM

(71) Applicant: CareFusion 303, Inc., San Diego, CA (US)

(72) Inventors: Vikas Gupta, Naperville, IL (US); Stephen J. Bollish, San Diego, CA (US); Gail Berglund, Carmel, IN (US); Timothy W. Vanderveen, Poway, CA (US); Alan Davison, San Diego, CA (US); Donald Halbert, San Diego, CA (US); Jesse J. Guerra, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/721,995

(22) Filed: May 26, 2015

(65) Prior Publication Data

US 2015/0250948 A1    Sep. 10, 2015

Related U.S. Application Data

(63) Continuation of application No. 13/802,679, filed on Mar. 13, 2013, now Pat. No. 9,069,887.

(51) Int. Cl.
*A61M 5/172* (2006.01)
*G06Q 50/22* (2018.01)
(Continued)

(52) U.S. Cl.
CPC ............ *A61M 5/172* (2013.01); *A61M 5/142* (2013.01); *A61M 5/1407* (2013.01);
(Continued)

(58) Field of Classification Search
CPC ............ G06F 19/3456; G06F 19/3468; G06F 19/326; A61M 5/16877; A61M 5/172;
(Continued)

(56) References Cited

U.S. PATENT DOCUMENTS 2,141,006 A    12/1938   Marinsky
3,724,455 A    4/1973    Unger
(Continued)

FOREIGN PATENT DOCUMENTS

CA    2472098 A1    7/2003
CA    2554903 A1    4/2005
(Continued)

OTHER PUBLICATIONS

U.S. Appl. No. 14/848,063, filed Sep. 8, 2015, Batch, et al. 20160000997.
(Continued)

*Primary Examiner* — An T Nguyen
(74) *Attorney, Agent, or Firm* — McDermott Will & Emery LLP

(57) ABSTRACT

Systems for use with a medical device for reducing medication errors are provided. In one aspect, a system includes a medical device that is configurable with operating limit parameters for providing medication to a patient, and a limiting system. The limiting system includes a memory that includes patient-specific information for the patient and a database includes acceptable operating parameters for providing the medication to the patient using the medical device, and a processor. The processor is configured to compare the acceptable operating parameters with the patient-specific information, and provide a modification of the operating limit parameters for providing the medication to the patient based on the comparison of the acceptable (Continued)

operating parameters with the patient-specific information. Methods and machine-readable media are also provided.

21 Claims, 4 Drawing Sheets

(51) Int. Cl.
 A61M 5/14 (2006.01)
 A61M 5/142 (2006.01)
 G06F 19/00 (2018.01)
(52) U.S. Cl.
 CPC ......... *G06F 19/3468* (2013.01); *G06Q 50/22* (2013.01); *A61M 2005/14208* (2013.01); *A61M 2205/52* (2013.01)
(58) Field of Classification Search
 CPC ............... A61M 5/142; A61M 5/1407; A61M 2005/14208; A61M 2205/52
 See application file for complete search history.

(56) References Cited

U.S. PATENT DOCUMENTS

| | | | |
|---|---|---|---|
| 3,831,006 A | 8/1974 | Chaffin, III et al. | |
| 3,848,112 A | 11/1974 | Weichselbaum et al. | |
| 3,872,448 A | 3/1975 | Mitchell, Jr. | |
| 3,898,984 A | 8/1975 | Mandel et al. | |
| 3,910,260 A | 10/1975 | Sarnoff et al. | |
| 3,921,196 A | 11/1975 | Patterson | |
| 3,970,996 A | 7/1976 | Yasaka et al. | |
| 4,051,522 A | 9/1977 | Healy et al. | |
| 4,135,241 A | 1/1979 | Stanis et al. | |
| 4,164,320 A | 8/1979 | Irazoqui et al. | |
| 4,216,462 A | 8/1980 | McGrath et al. | |
| 4,237,344 A | 12/1980 | Moore | |
| 4,315,309 A | 2/1982 | Coli | |
| 4,321,461 A | 3/1982 | Walter, Jr. et al. | |
| 4,360,125 A | 11/1982 | Martindale et al. | |
| 4,373,527 A | 2/1983 | Fischell | |
| 4,476,381 A | 10/1984 | Rubin | |
| 4,604,847 A | 8/1986 | Moulding, Jr. et al. | |
| 4,636,950 A | 1/1987 | Caswell et al. | |
| 4,674,652 A | 6/1987 | Aten et al. | |
| 4,676,776 A | 6/1987 | Howson | |
| 4,688,026 A | 8/1987 | Scribner et al. | |
| 4,695,954 A | 9/1987 | Rose et al. | |
| 4,696,671 A | 9/1987 | Epstein et al. | |
| 4,731,726 A | 3/1988 | Allen, III | |
| 4,733,364 A | 3/1988 | Yamagata | |
| 4,741,732 A | 5/1988 | Crankshaw et al. | |
| 4,756,706 A | 7/1988 | Kerns et al. | |
| 4,785,969 A | 11/1988 | McLaughlin | |
| 4,788,449 A | 11/1988 | Katz | |
| 4,803,625 A | 2/1989 | Fu et al. | |
| 4,810,243 A | 3/1989 | Howson | |
| 4,828,545 A | 5/1989 | Epstein et al. | |
| 4,831,562 A | 5/1989 | McIntosh et al. | |
| 4,835,372 A | 5/1989 | Gombrich et al. | |
| 4,839,806 A | 6/1989 | Goldfischer et al. | |
| 4,847,764 A | 7/1989 | Halvorson | |
| 4,850,009 A | 7/1989 | Zook et al. | |
| 4,853,521 A | 8/1989 | Claeys et al. | |
| 4,855,909 A | 8/1989 | Vincent et al. | |
| 4,857,713 A | 8/1989 | Brown | |
| 4,857,716 A | 8/1989 | Gombrich et al. | |
| 4,865,584 A | 9/1989 | Epstein et al. | |
| 4,882,575 A | 11/1989 | Kawahara | |
| 4,899,839 A | 2/1990 | Dessertine et al. | |
| 4,916,441 A | 4/1990 | Gombrich | |
| 4,918,604 A | 4/1990 | Baum | |
| 4,925,444 A | 5/1990 | Orkin et al. | |
| 4,942,544 A | 7/1990 | McIntosh et al. | |
| 4,950,246 A | 8/1990 | Muller | |
| 4,967,928 A | 11/1990 | Carter | |
| 4,970,669 A | 11/1990 | McIntosh et al. | |
| 4,978,335 A | 12/1990 | Arthur, III | |
| 5,001,630 A | 3/1991 | Wiltfong | |
| 5,006,699 A | 4/1991 | Felkner et al. | |
| 5,036,462 A | 7/1991 | Kaufman et al. | |
| 5,036,852 A | 8/1991 | Leishman | |
| 5,041,086 A | 8/1991 | Koenig et al. | |
| 5,072,383 A | 12/1991 | Brimm et al. | |
| 5,077,666 A | 12/1991 | Brimm et al. | |
| 5,078,683 A | 1/1992 | Sancoff et al. | |
| 5,088,981 A | 2/1992 | Howson et al. | |
| 5,088,056 A | 3/1992 | McIntosh et al. | |
| 5,100,380 A | 3/1992 | Epstein et al. | |
| 5,126,957 A | 6/1992 | Kaufman et al. | |
| 5,142,484 A | 6/1992 | Kaufman et al. | |
| 5,153,416 A | 10/1992 | Neeley | |
| 5,153,827 A | 10/1992 | Coutre et al. | |
| 5,164,575 A | 11/1992 | Neeley et al. | |
| 5,166,498 A | 11/1992 | Neeley | |
| 5,171,977 A | 12/1992 | Morrison | |
| 5,181,910 A | 1/1993 | Scanlon | |
| 5,190,522 A | 3/1993 | Wojcicki et al. | |
| 5,207,642 A | 5/1993 | Orkin et al. | |
| 5,235,507 A | 8/1993 | Sackler et al. | |
| 5,256,157 A | 10/1993 | Samiotes et al. | |
| 5,258,906 A | 11/1993 | Kroll et al. | |
| 5,265,010 A | 11/1993 | Evans-Paganelli et al. | |
| 5,267,174 A | 11/1993 | Kaufman et al. | |
| 5,291,399 A | 3/1994 | Chaco | |
| 5,292,029 A | 3/1994 | Pearson | |
| 5,307,263 A | 4/1994 | Brown | |
| 5,312,334 A | 5/1994 | Hara et al. | |
| 5,314,243 A | 5/1994 | McDonald et al. | |
| 5,315,505 A | 5/1994 | Pratt et al. | |
| 5,317,506 A | 5/1994 | Coutre et al. | |
| H1324 H | 6/1994 | Dalke et al. | |
| 5,331,547 A | 7/1994 | Laszlo | |
| 5,356,378 A | 10/1994 | Doan | |
| 5,367,555 A | 11/1994 | Isoyama | |
| 5,368,554 A | 11/1994 | Nazarian et al. | |
| 5,371,692 A | 12/1994 | Draeger et al. | |
| 5,374,813 A | 12/1994 | Shipp | |
| 5,376,070 A | 12/1994 | Purvis et al. | |
| 5,378,231 A | 1/1995 | Johnson et al. | |
| 5,382,232 A | 1/1995 | Hague et al. | |
| 5,390,238 A | 2/1995 | Kirk et al. | |
| 5,401,059 A | 3/1995 | Ferrario | |
| 5,404,384 A | 4/1995 | Colburn et al. | |
| 5,408,443 A | 4/1995 | Weinberger | |
| 5,412,372 A | 5/1995 | Parkhurst et al. | |
| 5,412,564 A | 5/1995 | Ecer | |
| 5,416,695 A | 5/1995 | Stutman et al. | |
| 5,456,691 A | 10/1995 | Snell | |
| 5,460,605 A | 10/1995 | Tuttle et al. | |
| 5,465,082 A | 11/1995 | Chaco | |
| 5,472,614 A | 12/1995 | Rossi | |
| 5,502,944 A | 4/1996 | Kraft et al. | |
| 5,515,426 A | 5/1996 | Yacenda et al. | |
| 5,522,798 A | 6/1996 | Johnson et al. | |
| 5,533,079 A | 7/1996 | Colburn et al. | |
| 5,536,084 A | 7/1996 | Curtis et al. | |
| 5,538,006 A | 7/1996 | Heim et al. | |
| 5,542,420 A | 8/1996 | Goldman et al. | |
| 5,544,649 A | 8/1996 | David et al. | |
| 5,544,661 A | 8/1996 | Davis et al. | |
| 5,547,470 A | 8/1996 | Johnson et al. | |
| 5,561,412 A | 10/1996 | Novak et al. | |
| 5,562,232 A | 10/1996 | Pearson | |
| 5,564,803 A | 10/1996 | McDonald et al. | |
| 5,573,506 A | 11/1996 | Vasko | |
| 5,582,593 A | 12/1996 | Hultman | |
| 5,583,758 A | 12/1996 | McIlroy et al. | |
| 5,592,374 A | 1/1997 | Fellegara et al. | |
| 5,594,786 A | 1/1997 | Chaco et al. | |
| 5,597,995 A | 1/1997 | Williams et al. | |
| 5,601,445 A | 2/1997 | Schipper et al. | |
| 5,622,429 A | 4/1997 | Heinze | |
| 5,628,309 A | 5/1997 | Brown | |
| 5,630,710 A | 5/1997 | Tune et al. | |

(56) References Cited

U.S. PATENT DOCUMENTS

| | | |
|---|---|---|
| 5,633,910 A | 5/1997 | Cohen |
| 5,643,212 A | 7/1997 | Coutre et al. |
| 5,644,778 A | 7/1997 | Burks et al. |
| 5,645,531 A | 7/1997 | Thompson et al. |
| 5,651,775 A | 7/1997 | Walker et al. |
| 5,655,118 A | 8/1997 | Heindel et al. |
| 5,657,236 A | 8/1997 | Conkright |
| 5,658,250 A | 8/1997 | Blomquist et al. |
| 5,672,154 A | 9/1997 | Sillen et al. |
| 5,681,285 A | 10/1997 | Ford et al. |
| 5,683,367 A | 11/1997 | Jordan et al. |
| 5,685,844 A | 11/1997 | Marttila |
| 5,689,229 A | 11/1997 | Chaco et al. |
| 5,692,640 A | 12/1997 | Caulfield et al. |
| 5,699,038 A | 12/1997 | Ulrich et al. |
| 5,700,998 A | 12/1997 | Palti |
| 5,703,786 A | 12/1997 | Conkright |
| 5,704,352 A | 1/1998 | Tremblay et al. |
| 5,710,551 A | 1/1998 | Ridgeway |
| 5,712,913 A | 1/1998 | Chaum |
| 5,713,856 A | 2/1998 | Eggers et al. |
| 5,721,913 A | 2/1998 | Ackroff et al. |
| 5,733,259 A | 3/1998 | Valcke et al. |
| 5,737,539 A | 4/1998 | Edelson et al. |
| 5,738,102 A | 4/1998 | Lemelson |
| 5,752,235 A | 5/1998 | Kehr et al. |
| 5,758,095 A | 5/1998 | Albaum et al. |
| 5,758,096 A | 5/1998 | Barsky et al. |
| 5,760,704 A | 6/1998 | Barton et al. |
| 5,764,034 A | 6/1998 | Bowman et al. |
| 5,772,585 A | 6/1998 | Lavin et al. |
| 5,774,865 A | 6/1998 | Glynn |
| 5,781,442 A | 7/1998 | Engleson et al. |
| 5,790,409 A | 8/1998 | Fedor et al. |
| 5,795,327 A | 8/1998 | Wilson et al. |
| 5,803,906 A | 9/1998 | Pratt et al. |
| 5,807,321 A | 9/1998 | Stoker et al. |
| 5,807,336 A | 9/1998 | Russo et al. |
| 5,819,229 A | 10/1998 | Boppe |
| 5,822,418 A | 10/1998 | Yacenda et al. |
| 5,822,544 A | 10/1998 | Chaco et al. |
| 5,832,488 A | 11/1998 | Eberhardt |
| 5,833,599 A | 11/1998 | Schrier et al. |
| 5,842,173 A | 11/1998 | Strum et al. |
| 5,842,976 A | 12/1998 | Williamson |
| 5,845,253 A | 12/1998 | Rensimer et al. |
| 5,845,254 A | 12/1998 | Lockwood et al. |
| 5,845,255 A | 12/1998 | Mayaud |
| 5,845,264 A | 12/1998 | Nellhaus |
| 5,848,593 A | 12/1998 | McGrady et al. |
| 5,850,344 A | 12/1998 | Conkright |
| 5,852,408 A | 12/1998 | Christiansen et al. |
| 5,855,550 A | 1/1999 | Lai et al. |
| 5,867,821 A | 2/1999 | Ballantyne et al. |
| 5,871,465 A | 2/1999 | Vasko |
| 5,883,806 A | 3/1999 | Meador et al. |
| 5,885,245 A | 3/1999 | Lynch et al. |
| 5,894,273 A | 4/1999 | Meador et al. |
| 5,895,371 A | 4/1999 | Levitas et al. |
| 5,899,998 A | 5/1999 | McGauley et al. |
| 5,903,211 A | 5/1999 | Flego et al. |
| 5,905,653 A | 5/1999 | Higham et al. |
| 5,907,490 A | 5/1999 | Oliver |
| 5,911,132 A | 6/1999 | Sloane |
| 5,911,687 A | 6/1999 | Sato et al. |
| 5,912,818 A | 6/1999 | McGrady et al. |
| 5,920,054 A | 7/1999 | Uber, III |
| 5,920,263 A | 7/1999 | Huttenhoff et al. |
| 5,928,329 A | 7/1999 | Clark et al. |
| 5,930,145 A | 7/1999 | Yuyama et al. |
| 5,935,099 A | 8/1999 | Peterson et al. |
| 5,941,710 A | 8/1999 | Lampotang et al. |
| 5,942,986 A | 8/1999 | Shabot et al. |
| 5,950,630 A | 9/1999 | Portwood et al. |
| 5,950,632 A | 9/1999 | Reber et al. |
| 5,953,099 A | 9/1999 | Walach |
| 5,954,641 A | 9/1999 | Kehr et al. |
| 5,957,885 A | 9/1999 | Bollish et al. |
| 5,961,036 A | 10/1999 | Michael et al. |
| 5,961,446 A | 10/1999 | Beller et al. |
| 5,971,593 A | 10/1999 | McGrady |
| 5,985,371 A | 11/1999 | Fujioka et al. |
| 5,995,077 A | 11/1999 | Wilcox et al. |
| 6,000,828 A | 12/1999 | Leet |
| 6,003,006 A | 12/1999 | Colella et al. |
| 6,009,333 A | 12/1999 | Chaco |
| 6,017,318 A | 1/2000 | Gauthier et al. |
| 6,021,392 A | 2/2000 | Lester et al. |
| 6,024,699 A | 2/2000 | Surwit et al. |
| 6,032,155 A | 2/2000 | de la Huerga |
| 6,048,087 A | 4/2000 | Laurent et al. |
| 6,053,887 A | 4/2000 | Levitas et al. |
| 6,063,026 A | 5/2000 | Schauss et al. |
| 6,082,776 A | 7/2000 | Feinberg |
| 6,112,182 A | 8/2000 | Akers et al. |
| RE36,871 E | 9/2000 | Epstein et al. |
| 6,134,582 A | 10/2000 | Kennedy |
| 6,135,949 A | 10/2000 | Russo et al. |
| 6,202,923 B1 | 3/2001 | Boyer et al. |
| 6,228,057 B1 | 5/2001 | Vasko |
| 6,241,704 B1 | 6/2001 | Peterson et al. |
| 6,269,340 B1 | 7/2001 | Ford et al. |
| 6,282,441 B1 | 8/2001 | Raymond et al. |
| 6,290,681 B1 | 9/2001 | Brown |
| 6,292,698 B1 | 9/2001 | Duffin et al. |
| 6,302,844 B1 | 10/2001 | Walker et al. |
| 6,312,378 B1 | 11/2001 | Bardy |
| 6,314,556 B1 | 11/2001 | DeBusk et al. |
| 6,319,200 B1 | 11/2001 | Lai et al. |
| 6,322,502 B1 | 11/2001 | Schoenberg et al. |
| 6,338,007 B1 | 1/2002 | Broadfield et al. |
| 6,339,732 B1 | 1/2002 | Phoon et al. |
| 6,406,426 B1 | 6/2002 | Reuss et al. |
| 6,409,684 B1 | 6/2002 | Wilk |
| 6,421,650 B1 | 7/2002 | Goetz et al. |
| 6,493,747 B2 | 12/2002 | Simmon et al. |
| 6,519,569 B1 | 2/2003 | White et al. |
| 6,529,892 B1 | 3/2003 | Lambert |
| 6,540,672 B1 | 4/2003 | Simonsen et al. |
| 6,558,352 B1 | 5/2003 | Hogan |
| 6,571,128 B2 | 5/2003 | Lebel et al. |
| 6,581,606 B2 | 6/2003 | Kutzko et al. |
| 6,671,563 B1 | 12/2003 | Engelson et al. |
| 6,745,764 B2 | 6/2004 | Hickle |
| 6,757,898 B1 | 6/2004 | Ilsen et al. |
| 6,785,589 B2 | 8/2004 | Eggenberger et al. |
| 6,796,956 B2 | 9/2004 | Hartlaub et al. |
| 6,799,149 B2 | 9/2004 | Hartlaub |
| 6,847,861 B2 | 1/2005 | Lunak et al. |
| 6,856,247 B1 | 2/2005 | Wallace |
| 6,873,268 B2 | 3/2005 | Lebel et al. |
| 6,993,402 B2 | 1/2006 | Klass et al. |
| 7,034,691 B1 | 4/2006 | Rapaport et al. |
| 7,054,844 B2 | 5/2006 | Fletcher et al. |
| 7,060,059 B2 | 6/2006 | Keith et al. |
| 7,096,072 B2 | 8/2006 | Engleson et al. |
| 7,201,734 B2 | 4/2007 | Hickle |
| 7,204,823 B2 | 4/2007 | Estes et al. |
| 7,215,991 B2 | 5/2007 | Besson et al. |
| 7,229,430 B2 | 6/2007 | Hickle et al. |
| 7,230,529 B2 | 6/2007 | Ketcherside, Jr. et al. |
| 7,256,708 B2 | 8/2007 | Rosenfeld et al. |
| 7,263,492 B1 | 8/2007 | Suresh et al. |
| 7,379,885 B1 | 5/2008 | Zakim |
| 7,384,420 B2 | 6/2008 | Dycus et al. |
| 7,398,183 B2 | 7/2008 | Holland et al. |
| 7,421,709 B2 | 9/2008 | Watson et al. |
| 7,433,853 B2 | 10/2008 | Brockway et al. |
| 7,471,994 B2 | 12/2008 | Ford et al. |
| 7,526,769 B2 | 4/2009 | Watts, Jr. et al. |
| 7,587,415 B2 | 9/2009 | Gaurav et al. |
| 7,612,679 B1 | 11/2009 | Fackler et al. |
| 7,693,697 B2 | 4/2010 | Westenskow et al. |
| 7,769,601 B1 | 8/2010 | Bleser et al. |

(56) References Cited

U.S. PATENT DOCUMENTS

| | | | |
|---|---|---|---|
| 7,771,385 B2 | 8/2010 | Eggers et al. | |
| 7,771,386 B2 | 8/2010 | Eggers et al. | |
| 7,776,031 B2 | 8/2010 | Hartlaub et al. | |
| 7,787,946 B2 | 8/2010 | Stahmann et al. | |
| 7,796,045 B2 | 9/2010 | Spear et al. | |
| 7,835,927 B2 | 11/2010 | Schlotterbeck et al. | |
| 7,847,970 B1 | 12/2010 | McGrady | |
| 7,860,583 B2 | 12/2010 | Condurso et al. | |
| 7,962,544 B2 | 6/2011 | Torok et al. | |
| 7,970,550 B2 | 6/2011 | Arakelyan et al. | |
| 8,005,688 B2 | 8/2011 | Coffman et al. | |
| 8,024,200 B2 | 9/2011 | Jennings et al. | |
| 8,160,895 B2 | 4/2012 | Schmitt et al. | |
| 8,197,437 B2 | 6/2012 | Kalafut et al. | |
| 8,291,337 B2 | 10/2012 | Gannin et al. | |
| 8,340,792 B2 | 12/2012 | Condurso et al. | |
| 8,630,722 B2 | 1/2014 | Condurso et al. | |
| 8,689,008 B2 | 4/2014 | Rangadass et al. | |
| 8,761,906 B2 | 6/2014 | Condurso et al. | |
| 9,069,887 B2 | 6/2015 | Gupta et al. | |
| 2001/0037083 A1 | 11/2001 | Hartlaub et al. | |
| 2001/0044731 A1 | 11/2001 | Coffman et al. | |
| 2002/0010679 A1 | 1/2002 | Felsher | |
| 2002/0016568 A1 | 2/2002 | Lebel et al. | |
| 2002/0016923 A1 | 2/2002 | Knaus et al. | |
| 2002/0022973 A1 | 2/2002 | Sun et al. | |
| 2002/0026223 A1 | 2/2002 | Riff et al. | |
| 2002/0033548 A1 | 3/2002 | Brodkin et al. | |
| 2002/0035484 A1 | 3/2002 | McCormick | |
| 2002/0038392 A1 | 3/2002 | De La Huerga | |
| 2002/0042636 A1 | 4/2002 | Koshiol et al. | |
| 2002/0046346 A1 | 4/2002 | Evans | |
| 2002/0077849 A1 | 6/2002 | Baruch et al. | |
| 2002/0087114 A1 | 7/2002 | Hartlaub | |
| 2002/0116509 A1 | 8/2002 | DeLaHuerga | |
| 2002/0120350 A1 | 8/2002 | Klass et al. | |
| 2002/0169636 A1 | 11/2002 | Eggers et al. | |
| 2002/0198624 A1 | 12/2002 | Greenwald et al. | |
| 2003/0009244 A1 | 1/2003 | Engleson et al. | |
| 2003/0036683 A1 | 2/2003 | Kehr et al. | |
| 2003/0045858 A1 | 3/2003 | Struys et al. | |
| 2003/0051737 A1 | 3/2003 | Hickle et al. | |
| 2003/0063524 A1 | 4/2003 | Niemiec et al. | |
| 2003/0069481 A1 | 4/2003 | Hervy et al. | |
| 2003/0105389 A1 | 6/2003 | Noonan et al. | |
| 2003/0105555 A1 | 6/2003 | Lunak et al. | |
| 2003/0106553 A1 | 6/2003 | Vanderveen | |
| 2003/0114836 A1 | 6/2003 | Estes et al. | |
| 2003/0121517 A1 | 7/2003 | McFarland | |
| 2003/0129578 A1 | 7/2003 | Mault | |
| 2003/0135087 A1 | 7/2003 | Hickle et al. | |
| 2003/0135388 A1 | 7/2003 | Martucci et al. | |
| 2003/0139701 A1 | 7/2003 | White et al. | |
| 2003/0140928 A1 | 7/2003 | Bui et al. | |
| 2003/0140929 A1 | 7/2003 | Wilkes et al. | |
| 2003/0149599 A1 | 8/2003 | Goodall et al. | |
| 2003/0156143 A1 | 8/2003 | Westenskow et al. | |
| 2003/0158746 A1 | 8/2003 | Forrester | |
| 2003/0163223 A1 | 8/2003 | Blomquist | |
| 2003/0205897 A1 | 11/2003 | Kaufman | |
| 2003/0236683 A1 | 12/2003 | Henderson et al. | |
| 2004/0068229 A1 | 4/2004 | Jansen et al. | |
| 2004/0073329 A1 | 4/2004 | Engleson et al. | |
| 2004/0107118 A1 | 6/2004 | Harnsberger et al. | |
| 2004/0122702 A1 | 6/2004 | Sabol et al. | |
| 2004/0122705 A1 | 6/2004 | Sabol et al. | |
| 2004/0122719 A1 | 6/2004 | Sabol et al. | |
| 2004/0122790 A1 | 6/2004 | Walker et al. | |
| 2004/0128162 A1 | 7/2004 | Schlotterbeck et al. | |
| 2004/0152622 A1 | 8/2004 | Keith et al. | |
| 2004/0167465 A1 | 8/2004 | Mihai et al. | |
| 2004/0167804 A1 | 8/2004 | Simpson et al. | |
| 2004/0172283 A1 | 9/2004 | Vanderveen et al. | |
| 2004/0172300 A1 | 9/2004 | Mihai et al. | |
| 2004/0172302 A1 | 9/2004 | Martucci et al. | |
| 2004/0176297 A1 | 9/2004 | Cheung et al. | |
| 2004/0188998 A1 | 9/2004 | Henthorn | |
| 2004/0193325 A1 | 9/2004 | Bonderud et al. | |
| 2004/0193446 A1 | 9/2004 | Mayer et al. | |
| 2004/0260478 A1 | 12/2004 | Schwamm | |
| 2005/0010166 A1 | 1/2005 | Hickle | |
| 2005/0010269 A1 | 1/2005 | Lebel et al. | |
| 2005/0020996 A1 | 1/2005 | Hartlaub et al. | |
| 2005/0021297 A1 | 1/2005 | Hartlaub | |
| 2005/0022274 A1 | 1/2005 | Campbell et al. | |
| 2005/0033606 A1 | 2/2005 | Miller | |
| 2005/0049179 A1 | 3/2005 | Davidson et al. | |
| 2005/0055242 A1 | 3/2005 | Bello et al. | |
| 2005/0088296 A1 | 4/2005 | Lee | |
| 2005/0096941 A1 | 5/2005 | Tong | |
| 2005/0097566 A1 | 5/2005 | Watts et al. | |
| 2005/0107914 A1 | 5/2005 | Engleson et al. | |
| 2005/0108057 A1 | 5/2005 | Cohen et al. | |
| 2005/0113945 A1 | 5/2005 | Engleson et al. | |
| 2005/0119788 A1 | 6/2005 | Engleson et al. | |
| 2005/0144043 A1* | 6/2005 | Holland | G06F 19/326 705/3 |
| 2005/0145010 A1 | 7/2005 | Vanderveen et al. | |
| 2005/0148890 A1 | 7/2005 | Hastings | |
| 2005/0171815 A1 | 8/2005 | Vanderveen | |
| 2005/0224083 A1 | 10/2005 | Crass et al. | |
| 2005/0278194 A1 | 12/2005 | Holland et al. | |
| 2006/0026205 A1 | 2/2006 | Butterfield | |
| 2006/0047538 A1 | 3/2006 | Condurso et al. | |
| 2006/0053036 A1 | 3/2006 | Coffman et al. | |
| 2006/0079831 A1 | 4/2006 | Gilbert | |
| 2006/0101072 A1 | 5/2006 | Busche et al. | |
| 2006/0122481 A1 | 6/2006 | Sievenpiper et al. | |
| 2006/0190302 A1 | 8/2006 | Eggers et al. | |
| 2006/0200369 A1 | 9/2006 | Batch et al. | |
| 2006/0206356 A1 | 9/2006 | Vanderveen | |
| 2006/0217628 A1 | 9/2006 | Huiku | |
| 2006/0218015 A1 | 9/2006 | Walker et al. | |
| 2006/0229551 A1 | 10/2006 | Martinez et al. | |
| 2006/0249423 A1 | 11/2006 | Reijonen | |
| 2006/0271401 A1 | 11/2006 | Lassetter et al. | |
| 2006/0287890 A1 | 12/2006 | Stead et al. | |
| 2007/0015972 A1 | 1/2007 | Wang et al. | |
| 2007/0043767 A1 | 2/2007 | Osborne et al. | |
| 2007/0061266 A1 | 3/2007 | Moore et al. | |
| 2007/0061393 A1 | 3/2007 | Moore | |
| 2007/0083389 A1 | 4/2007 | Dyer et al. | |
| 2007/0106457 A1 | 5/2007 | Rosenberg | |
| 2007/0106753 A1 | 5/2007 | Moore | |
| 2007/0106754 A1 | 5/2007 | Moore | |
| 2007/0129647 A1 | 6/2007 | Lynn | |
| 2007/0156452 A1 | 7/2007 | Batch | |
| 2007/0156860 A1 | 7/2007 | Nedelcu et al. | |
| 2007/0168301 A1 | 7/2007 | Eisner et al. | |
| 2007/0208454 A1 | 9/2007 | Forrester et al. | |
| 2007/0210157 A1 | 9/2007 | Miller | |
| 2007/0286466 A1 | 12/2007 | Heffernan et al. | |
| 2007/0293843 A1 | 12/2007 | Ireland et al. | |
| 2008/0015549 A1 | 1/2008 | Maughan | |
| 2008/0025230 A1 | 1/2008 | Patel et al. | |
| 2008/0034323 A1* | 2/2008 | Blomquist | A61M 5/172 715/810 |
| 2008/0040151 A1 | 2/2008 | Moore | |
| 2008/0046292 A1 | 2/2008 | Myers | |
| 2008/0141272 A1 | 6/2008 | Borgendale et al. | |
| 2008/0162254 A1 | 7/2008 | Herger et al. | |
| 2008/0164998 A1 | 7/2008 | Scherpbier et al. | |
| 2008/0169045 A1 | 7/2008 | Tribble et al. | |
| 2008/0195246 A1 | 8/2008 | Tribble et al. | |
| 2008/0272138 A1 | 11/2008 | Ross et al. | |
| 2008/0317672 A1 | 12/2008 | Viertio-Oja | |
| 2009/0012812 A1 | 1/2009 | Rausch et al. | |
| 2009/0012813 A1 | 1/2009 | Berzansky et al. | |
| 2009/0099867 A1 | 4/2009 | Newman | |
| 2009/0112333 A1 | 4/2009 | Sahai | |
| 2009/0125335 A1 | 5/2009 | Manetta et al. | |
| 2009/0150484 A1 | 6/2009 | Roberts | |
| 2009/0210252 A1 | 8/2009 | Silver | |
| 2009/0240651 A1 | 9/2009 | Fletcher et al. | |

(56) References Cited

U.S. PATENT DOCUMENTS

| | | |
|---|---|---|
| 2009/0306585 A1 | 12/2009 | Pang et al. |
| 2009/0306944 A1 | 12/2009 | Willmann et al. |
| 2009/0319623 A1 | 12/2009 | Srinivasan et al. |
| 2010/0037067 A1 | 2/2010 | Rangadass et al. |
| 2010/0094653 A1 | 4/2010 | Tribble et al. |
| 2010/0121654 A1* | 5/2010 | Portnoy .......... G06F 19/325 |
| | | 705/3 |
| 2010/0161113 A1 | 6/2010 | Tribble et al. |
| 2010/0169120 A1 | 7/2010 | Herbst et al. |
| 2010/0169771 A1 | 7/2010 | Pelegrin et al. |
| 2010/0174552 A1 | 7/2010 | Hawkes et al. |
| 2010/0174553 A1 | 7/2010 | Kaufman et al. |
| 2010/0179825 A1 | 7/2010 | Hanov et al. |
| 2010/0241453 A1 | 9/2010 | Malec |
| 2010/0241456 A1* | 9/2010 | Miller ............... G06Q 50/24 |
| | | 705/3 |
| 2010/0271218 A1 | 10/2010 | Hoag et al. |
| 2010/0280840 A1 | 11/2010 | Fukushi et al. |
| 2010/0323397 A1 | 12/2010 | Reavy et al. |
| 2011/0015941 A1 | 1/2011 | Backhaus |
| 2011/0046975 A1 | 2/2011 | Hoffman |
| 2011/0060758 A1 | 3/2011 | Schlotterbeck et al. |
| 2011/0078608 A1 | 3/2011 | Gannon et al. |
| 2011/0119612 A1 | 5/2011 | Gannon et al. |
| 2011/0179405 A1 | 7/2011 | Dicks et al. |
| 2011/0202495 A1 | 8/2011 | Gawlick |
| 2011/0282691 A1 | 11/2011 | Coffman et al. |
| 2011/0288882 A1 | 11/2011 | Halow |
| 2011/0313787 A1 | 12/2011 | Rangadass et al. |
| 2012/0011253 A1 | 1/2012 | Friedman et al. |
| 2012/0016215 A1 | 1/2012 | Condurso et al. |
| 2012/0041775 A1* | 2/2012 | Cosentino .......... G06F 19/3418 |
| | | 705/2 |
| 2012/0053533 A1 | 3/2012 | Butterfield et al. |
| 2012/0075061 A1 | 3/2012 | Barnes |
| 2012/0136673 A1 | 5/2012 | Presley et al. |
| 2012/0173264 A1 | 7/2012 | Brush et al. |
| 2012/0179006 A1 | 7/2012 | Jansen et al. |
| 2012/0182939 A1 | 7/2012 | Rajan et al. |
| 2012/0185267 A1 | 7/2012 | Kamen et al. |
| 2012/0191052 A1 | 7/2012 | Rao |
| 2012/0239824 A1 | 9/2012 | Nguyen et al. |
| 2012/0241043 A1 | 9/2012 | Perazzo et al. |
| 2012/0247480 A1 | 10/2012 | Varga |
| 2012/0253835 A1 | 10/2012 | Tracy et al. |
| 2012/0265549 A1 | 10/2012 | Virolainen |
| 2013/0018356 A1 | 1/2013 | Prince et al. |
| 2013/0085771 A1 | 4/2013 | Ghanbari et al. |
| 2013/0096444 A1 | 4/2013 | Condurso et al. |
| 2013/0197927 A1 | 8/2013 | Vanderveen et al. |
| 2013/0197928 A1 | 8/2013 | Vanderveen et al. |
| 2013/0197929 A1 | 8/2013 | Vanderveen et al. |
| 2013/0197930 A1 | 8/2013 | Garibaldi et al. |
| 2013/0197931 A1 | 8/2013 | Gupta et al. |
| 2013/0204433 A1 | 8/2013 | Gupta et al. |
| 2013/0204637 A1 | 8/2013 | Vanderveen et al. |
| 2013/0262138 A1 | 10/2013 | Jaskela et al. |
| 2014/0028464 A1 | 1/2014 | Garibaldi |
| 2014/0100868 A1 | 4/2014 | Condurso et al. |
| 2014/0278466 A1 | 9/2014 | Simmons et al. |
| 2014/0297313 A1 | 10/2014 | Condurso et al. |
| 2014/0350950 A1 | 11/2014 | Jaskela et al. |
| 2015/0250948 A1 | 9/2015 | Gupta et al. |
| 2016/0000997 A1 | 1/2016 | Batch et al. |

FOREIGN PATENT DOCUMENTS

| | | |
|---|---|---|
| CN | 1759398 A | 4/2006 |
| CN | 101116077 A | 1/2008 |
| CN | 101146055 A | 3/2008 |
| CN | 201110955 Y | 9/2008 |
| CN | 101331491 A | 12/2008 |
| CN | 101890193 A | 11/2010 |
| CN | 102068725 A | 5/2011 |
| CN | 10 2521394 A | 6/2012 |
| CN | 102508877 A | 6/2012 |
| CN | 102688532 A | 9/2012 |
| CN | 102799783 A | 11/2012 |
| DE | 4023785 A1 | 1/1992 |
| EP | 0192786 A2 | 9/1986 |
| EP | 0384155 A2 | 8/1990 |
| EP | 0595474 A2 | 5/1994 |
| EP | 0649316 A1 | 4/1995 |
| EP | 0652528 A2 | 5/1995 |
| EP | 0784283 A1 | 7/1997 |
| EP | 0921488 A1 | 6/1999 |
| EP | 1003121 A2 | 5/2000 |
| EP | 1018347 A2 | 7/2000 |
| EP | 1237113 A2 | 9/2002 |
| GB | 2 141 006 A | 12/1984 |
| JP | S62114562 | 5/1987 |
| JP | H11505352 | 5/1999 |
| JP | 2002520718 A | 7/2002 |
| JP | 2003085283 A | 3/2003 |
| JP | 2004287616 A | 10/2004 |
| JP | 2006155070 A | 6/2006 |
| JP | 2008508616 A | 3/2008 |
| JP | H5168708 B2 | 3/2013 |
| KR | 102007004561 | 5/2007 |
| KR | 1020080013129 | 2/2008 |
| KR | 100847397 B1 | 7/2008 |
| KR | 1020100125972 | 12/2010 |
| KR | 1020110070824 | 6/2011 |
| KR | 1020120076615 | 7/2012 |
| KR | 1020120076635 | 7/2012 |
| NZ | 522631 A | 7/2004 |
| WO | WO-1993022735 A1 | 11/1993 |
| WO | WO-1994005344 A1 | 3/1994 |
| WO | WO-2000003344 | 3/1994 |
| WO | WO-1994008647 A1 | 4/1994 |
| WO | WO-1994013250 A1 | 6/1994 |
| WO | WO-1995023378 A2 | 8/1995 |
| WO | WO-1996020745 A1 | 7/1996 |
| WO | WO-1996025214 A1 | 8/1996 |
| WO | WO-1996036923 A1 | 11/1996 |
| WO | WO-1997004712 A1 | 2/1997 |
| WO | WO-1998013783 A1 | 4/1998 |
| WO | WO-1998028676 A2 | 7/1998 |
| WO | WO-1999009505 A1 | 2/1999 |
| WO | WO-1999010829 A1 | 3/1999 |
| WO | WO-1999010830 A1 | 3/1999 |
| WO | WO-1999035588 A1 | 7/1999 |
| WO | WO-1999044167 A1 | 9/1999 |
| WO | WO-1999045490 A2 | 9/1999 |
| WO | WO-1999046718 A1 | 9/1999 |
| WO | WO-1999067732 A1 | 12/1999 |
| WO | WO-2000004521 | 1/2000 |
| WO | WO-2000018449 | 4/2000 |
| WO | WO-2000032088 | 6/2000 |
| WO | WO-2000032098 | 6/2000 |
| WO | WO-2001086506 | 11/2001 |
| WO | WO-2001088828 | 11/2001 |
| WO | WO-2002036044 | 5/2002 |
| WO | WO-2002069099 | 9/2002 |
| WO | WO-2003038566 | 5/2003 |
| WO | WO-2003053503 | 7/2003 |
| WO | WO-2003092769 | 11/2003 |
| WO | WO-2003094091 | 11/2003 |
| WO | WO-2004060443 A2 | 7/2004 |
| WO | WO-2004061745 A2 | 7/2004 |
| WO | WO-2010124016 A1 | 10/2010 |
| WO | WO-2010124328 A1 | 11/2010 |
| WO | WO-2012095829 A2 | 7/2012 |

OTHER PUBLICATIONS

U.S. Appl. No. 09/860,865, filed May 18, 2001, Damon J. Coffman, et al.

U.S. Appl. No. 10/750,032, filed Dec. 31, 2003, Timothy W. Vanderveen.

U.S. Appl. No. 10/361,704, filed Feb. 9, 2003, Timothy W. Vanderveen, et al.

(56) References Cited

OTHER PUBLICATIONS

U.S. Appl. No. 13/185,427, filed Jul. 18, 2011, Damon J. Coffman, et al.
U.S. Appl. No. 13/246,782, filed Sep. 27, 2011, Joseph Condurso, et al.
U.S. Appl. No. 13/559,537, filed Jul. 26, 2012, Federico Garibaldi.
U.S. Appl. No. 13/802,663, filed Mar. 13, 2013, Federico Garibaldi.
U.S. Appl. No. 13/802,443, filed Mar. 13, 2013, Timothy W. Vanderveen, et al.
U.S. Appl. No. 13/802,683, filed Mar. 13, 2013, Vikas Gupta, et al.
U.S. Appl. No. 13/802,433, filed Mar. 13, 2013, Timothy W. Vanderveen, et al.
U.S. Appl. No. 13/802,454, filed Mar. 13, 2013, Timothy W. Vanderveen, et al.
U.S. Appl. No. 13/901,504, filed May 23, 2013, Maria Consolacion Jaskela, et al.
U.S. Appl. No. 14/306,125, filed Jun. 16, 2014, Joseph Condurso, et al.
U.S. Appl. No. 11/326,145, filed Dec. 30, 2005, Richard M. Batch, et al.
U.S. Appl. No. 13/421,776, filed Mar. 15, 2012, Ryan Nguyen, et al.
U.S. Appl. No. 13/802,446, filed Mar. 13, 2013, Timothy W. Vanderveen, et la.
U.S. Appl. No. 13/901,501, filed May 23, 2013, Maria Consolacion Jaskela, et al.
U.S. Appl. No. 90/009,912, filed Aug. 12, 2013, Schlotterbeck et al.
U.S. Appl. No. 90/011,697, filed Aug. 12, 2013, Schlotterbeck et al.
"General-Purpose Infusion Pumps," Evaluation—Health Devices, Oct. 2002, pp. 353-387, vol. 31 (10), ECRI Institute.
"Infusion Pump Technology," Health Devices, Apr.-May 1998, pp. 150-170, vol. 27(4-5), ECRI Institute.
"Infusion Pumps, General Purpose," Healthcare Product Comparison System, 2007, pp. 1-54, ECRI Institute.
"Infusion Pumps, Large-Volume," Healthcare Product Comparison System, 2010, pp. 1-51, ECRI Institute.
"Smart Infusion Pumps Join CPOE and Bar Coding as Important Ways to Prevent Medication Errors," ISMP—Medication Safety Alert, Feb. 7, 2002, 2 pgs., Institute for Safe Medication Practices.
Anonymous, Guardrails® Safety Software—Medley TM Medication Safety System, Alaris Medical Systems XP-00234431; 2002 Alaris Medical Systems Inc. Nov. 2002, SSM @2159C.
Baldauf-Sobez et al., "How Siemens' Computerized Physician Order Entry Helps Prevent the Human Errors," electromedica, vol. 71, No. 1, 2003, pp. 2-10.
Eskew, James et al., Using Innovative Technologies to Set New Safety Standards for the Infusion of Intravenous Medications, Hospital Pharmacy, vol. 37, No. 11, pp. 1179-1189, 2002, Facts and Comparisons.
Kohn, et al., "To Err is Human—Building a Safer Health System," National Academy Press, 2002, pp. i-287, National Academy of Sciences.
Lesar, "Recommendations for Reducing Medication Errors," Medscape Pharmacists, posted Jul. 24, 2000, 10 pgs, vol. 1(2), Medscape Pharmacists, <http://www.medscape.com>.
Meier, "Hospital Products Get Seal of Approval at a Price," The New York Times, Apr. 23, 2002, 5 pgs.
Queensland Health. Use of returned or unused dispensed medicines, Jan. 5, 2005, Queensland Government. pp. 1-2.
Shabot et al., "Wireless clinical alerts for critical medication, laboratory and physiologic data," System Sciences 2000. Proceedings of the 33rd Annual Conference on Jan. 4-7, 2000, Piscataway, NJ, IEEE, Jan. 4, 2000.
Williams, et al., "Reducing the Risk of User Error with Infusion Pumps," Professional Nurse—Safe Practice—Infusion Devices, Mar. 2000, pp. 382-384, vol. 15(6).

Yokoi, "Prevention of Errors in Injection/Drip Infusion—No excuse for ignorance!—Essential Points of Accident Prevention, IV Infusion Pump, Syringe-pump Accident Prevention," JIN Special, Igaku Shoin K.K., Dec. 1, 2001, pp. 109-120, No. 70.
Extended European Search Report for Application No. 14775918.7, dated Sep. 13, 2016, 10 pages.
Extended European Search Report for Application No. 14779655.1, dated Jul. 14, 2016, 8 pages.
Extended European Search Report for Application No. 14780320.9, dated Jul. 1, 2016, 7 pages.
Canadian Office Action for Application No. 2512991, dated Mar. 2, 2017, 4 pages.
Extended European Search Report for Application No. 14801726.2, dated Jan. 5, 2017, 8 pages.
Chinese Office Action for Application No. 201480015147.6, dated Mar. 10, 2017, 10 pages excluding translation.
Evans, R. S. et al., "Enhanced notification of infusion pump programming errors", Studies in health technology and informatics, Jan. 1, 2010, pp. 734-738, XP055305644, Netherlands DOI: 10.3233/978-1-60750-588-4-734 Retrieved from the Internet: URL:http://booksonline.iospress.nl/Extern/EnterMedLine.aspx?ISSN=0926-9630&Volume=160&SPage=734 [retrieved on Sep. 26, 2016].
Extended European Search Report and Written Opinion for Application No. 14772937.0, dated Oct. 10, 2016, 9 pages.
Extended European Search Report and Written Opinion for Application No. 14779139.6, dated Nov. 7, 2016, 7 pages.
Extended European Search Report for Application No. 14801713.0, dated Jan. 16, 2017, 8 pages.
European Office Action for Application No. 14779655.1, dated Jul. 28, 2017, 6 pages.
Memo concerning Mexican Office Action for Application No. MX/a/2015/015959, dated Sep. 21, 2017, 4 pages.
Canadian Office Action for Application No. 2551903, dated Mar. 28, 2017, 7 pages.
European Office Action for Application No. 12756903.6, dated Apr. 19, 2017, 5 pages.
Office Action for United Arab Emirates Application No. UAE/P/0962/2013, dated Apr. 17, 2017, 18 pages.
Australian Examination Report No. 1 for Application No. 2016216550, dated Sep. 20, 2017, 3 pages.
Chinese Office Action for Application No. 201480015147.6, dated Nov. 16, 2017, 8 pages.
European Communication of the Board of Appeal for Application No. 05791269.3, dated Nov. 10, 2017, 7 pages.
European Office Action for Application No. 14775918.7, dated Dec. 20, 2017, 8 pages.
Chinese Office Action for Application No. 201480015025.7, dated Jan. 23, 2018, 11 pages excluding English summary.
Chinese Office Action for Application No. 201480015036.5, dated Jan. 23, 2018, 13 pages excluding English translation.
European Office Action for Application No. 14779655.1, dated Mar. 8, 2018, 7 pages.
Japanese Office Action in Application No. 2016-501081, dated Feb. 9, 2018, 4 pages.
Memo concerning Mexican Office Action for Application No. MX/a/2015/015959, memo dated Mar. 2, 2018, 1 page.
Canadian Office Action for Application No. 2512991, dated Jan. 10, 2018, 4 pages.
Canadian Office Action for Application No. 2828898, dated Jan. 11, 2018, 8 pages.
Canadian Office Action for Application No. 2551903, dated Mar. 5, 2018, 8 pages.
Chinese Office Action for Application No. 201480015147.6, dated May 3, 2018, 6 pages.
European Office Action for Application No. 14772937.0, dated Apr. 19, 2018, 9 pages.

* cited by examiner

PATIENT-SPECIFIC MEDICATION MANAGEMENT SYSTEM

CROSS-REFERENCE TO RELATED APPLICATIONS

The present application is a continuation of U.S. application Ser. No. 13/802,679, filed Mar. 13, 2013, entitled "Patient-Specific Medication Management System", the disclosure of which is hereby incorporated by reference in its entirety for all purposes.

BACKGROUND

Field

The present disclosure relates generally to systems and methods for managing patient care in a health care facility, and more particularly, to systems and methods for integrating and managing information with respect to medical care, medication delivery, asset identification, and verification of drug delivery.

Description of the Related Art

Medication errors, that is, errors that occur in the ordering, dispensing, and administration of medications, regardless of whether those errors cause injury or not, are a significant consideration in the delivery of healthcare in the institutional setting. Additionally, adverse drug events (ADE), which are defined as injuries involving a drug that require medical intervention and are a subset of medication errors, represent some of the most serious medication errors are responsible for a number of patient injuries and death.

Healthcare facilities continually search for ways to reduce the occurrence and severity of medication errors. Various systems and methods are commonly used to reduce the frequency of occurrence and severity of preventable adverse drug events (PADE) and other medication errors. In the administration of medication, focus is typically directed to the following five "rights" or factors: the right patient, the right drug, the right route, the right amount, and the right time. Systems and methods seeking to reduce ADEs and PADEs should take these five rights into consideration.

Delivery, verification, and control of medication in an institutional setting have traditionally been areas where errors can occur. In a typical healthcare facility, a physician enters an order for a medication for a particular patient. This order may be handled either as a simple handwritten order, or it may be entered into an automated system, such as a physician order entry (POE) system. The handwritten order or the electronic prescription from the POE system is routed to the pharmacy, where the order is filled. Typically, pharmacies check the physician order against possible allergies of the patient and for possible drug interactions in the case where two or more drugs are prescribed, and also check for contraindications. Depending on the healthcare facility, the medication may be identified and gathered within the pharmacy and placed into a transport carrier for transport to a nurse station. Once at the nurse station, the prescriptions are again checked against the medications that have been identified for delivery to ensure that no errors have occurred.

Such a system works well to verify that patients are receiving the appropriate drug when drugs are delivered orally. But the system may not be capable of thoroughly verifying that the correct administration of an intravenous (IV) drug is being provided to a patient. Incorrect administration of the medication may occur where the medication is to be administered using an automated or semi-automated administration device, such as an infusion pump (e.g., including large volume infusion or syringe type pumps), if the automated device is programmed with incorrect medication administration parameters. For example, even where the medication order includes the correct infusion parameters, those parameters may be incorrectly entered into an infusion pump, causing the infusion pump to administer the medication in a manner that may not result in the prescribed treatment. Furthermore, if the infusion pump is configured with certain operating limit parameters, the operating limit parameters may reflect values that are generally considered safe for a typical patient but that may be unsafe for the patient to whom the medication is being delivered.

SUMMARY

According to one embodiment of the present disclosure, a system for use with a medical device for reducing medication errors is provided. The system includes a medical device that is configurable with operating limit parameters for providing medication to a patient, and a limiting system. The limiting system includes a memory that includes patient-specific information for the patient and a database includes acceptable operating parameters for providing the medication to the patient using the medical device, and a processor. The processor is configured to compare the acceptable operating parameters with the patient-specific information, and provide a modification of the operating limit parameters for providing the medication to the patient based on the comparison of the acceptable operating parameters with the patient-specific information.

In certain aspects of the system, the medical device is configurable with operating limit parameters for providing a mixture includes a plurality of medications to a patient, and the database includes acceptable operating parameters for providing the mixture to the patient using the medical device. The patient-specific information can include laboratory data for the patient. The laboratory data can include at least one of a blood coagulation measure, a vitamin level, a platelet count value, a thromboplastin time, or a serum level. The patient-specific information can include at least one of a medication ordered for the patient, a time at which the medication is ordered for the patient, a treatment plan for the patient, a medication resistance of the patient, a weight of the patient, a height of the patient, a body surface area of the patient, an age of the patient, a gender of the patient, or an ethnicity of the patient. In certain aspects of the system, the processor being configured to compare the acceptable operating parameters with the patient-specific information includes the processor comparing a first weight of the patient provided to the medical device with a second weight of the patient provided to another medical device. In certain aspects of the system, the processor being configured to provide the modification of the operating limit parameters for providing the medication to the patient includes the processor being configured to modify the operating limit parameters based on a determination of the acceptable operating parameters for a person having the patient's body surface area. The acceptable operating parameters can include a plurality of rules indicating whether the patient-specific information includes a value that is within or exceeds a threshold define by at least one of the plurality of rules. At least one of the rules can indicate a maximum total amount of the medication to provide to the patient over a period of time. The medical device can include an infusion pump. The operating limit parameters can include at least one of a rate at which to provide the medication, an amount of the medication to provide, and a length of time to provide the medication. In certain aspects of the system, the processor being configured to provide the modification of the operating limit parameters based on the patient-specific information includes the processor being configured to define at least one of a maximum value or minimum value for at least one operating limit parameter associated with delivery of the medication to the patient based on the patient-specific information. In certain aspects of the system, the processor being configured to provide the modification of the operating limit parameters based on the patient-specific information includes the processor being configured to define at least one of a pair of a soft maximum value that can be exceeded and a hard maximum value that cannot be exceeded, and a soft minimum value that can be exceeded and a hard minimum value that cannot be exceeded for at least one operating limit parameter associated with delivery of the medication to the patient based on the patient-specific information. The processor can further be configured to provide a notification to the medical device indicating that the operating limit parameters for providing the medication to the patient have been modified based on the patient-specific information. The processor can further be configured to receive an input from a caregiver to override the modification of the operating limit parameters. The input from the caregiver can include an indication why the caregiver overrode the modification of the operating limit parameters. The processor can further be configured to record when the caregiver overrides the modification of the operating limit parameters. The processor can further be configured to receive configuration parameters for determining whether to provide the notification to the medical device based on at least one of an identity of a caregiver, identification of a location of the medical device, or an institutional preference. The patient-specific information can be received from an external data system in a native message format of the external data system and converted into an internal messaging format configured for use with the limiting system.

According to another embodiment of the present disclosure, a method for use with a medical device to reduce medication errors is provided. The method includes receiving patient-specific information for a patient, and comparing the patient-specific information with a database includes acceptable operating parameters for a medical device. The method also includes providing a modification of operating limit parameters of the medical device for providing a medication to the patient based on the comparison of the patient-specific information with the acceptable operating parameters.

In certain aspects of the method, the medical device is configurable with operating limit parameters for providing a mixture includes a plurality of medications to a patient, and the database includes acceptable operating parameters for providing the mixture to the patient using the medical device. The patient-specific information can include laboratory data for the patient. The laboratory data can include at least one of a blood coagulation measure, a vitamin level, a platelet count value, a thromboplastin time, or a plasma/serum concentration of medication, or other physiologic component, such as electrolyte concentration. The patient-specific information can include at least one of a medication ordered for the patient, a time at which the medication is ordered for the patient, a treatment plan for the patient, a medication resistance of the patient, a weight of the patient, a height of the patient, a body surface area of the patient, an age of the patient, a gender of the patient, genetic makeup of the patient, or an ethnicity of the patient. Comparing the acceptable operating parameters with the patient-specific information can include comparing a first weight of the patient provided to the medical device with a second weight of the patient provided to another medical device. Providing the modification of the operating limit parameters for providing the medication to the patient can include modifying the operating limit parameters based on a determination of the acceptable operating parameters for a person having the patient's body surface area. The acceptable operating parameters can include a plurality of rules indicating whether the patient-specific information can include a value that is within or exceeds a threshold define by at least one of the plurality of rules. At least one of the rules can indicate a maximum total amount of the medication to provide to the patient over a period of time. The medical device can include an infusion pump. The operating limit parameters can include at least one of a rate at which to provide the medication, an amount of the medication to provide, and a length of time to provide the medication. In certain aspects of the method, providing the modification of the operating limit parameters based on the patient-specific information can include defining at least one of a maximum value or minimum value for at least one operating limit parameter associated with delivery of the medication to the patient based on the patient-specific information. In certain aspects of the method, providing the modification of the operating limit parameters based on the patient-specific information can include defining at least one of a pair of a soft maximum value that can be exceeded and a hard maximum value that cannot be exceeded, or a soft minimum value that can be exceeded and a hard minimum value that cannot be exceeded for at least one operating limit parameter associated with delivery of the medication to the patient based on the patient-specific information. In certain aspects of the method, the method further includes providing a notification to the medical device indicating that the operating limit parameters for providing the medication to the patient have been modified based on the patient-specific information. The method can further include receiving an input from a caregiver to override the modification of the operating limit parameters. The input from the caregiver can include an indication why the caregiver overrode the modification of the operating limit parameters. The method can further include recording when the caregiver overrides the modification of the operating limit parameters. The method can further include receiving configuration parameters for determining whether to provide the notification to the medical device based on at least one of an identity of a caregiver, identification of a location of the medical device, or an institutional preference. The operating limit parameters of the medical device can be modified by a limiting system, and the patient-specific information can be received from an external data system in a native message format of the external data system and converted into an internal messaging format configured for use with the limiting system.

According to one embodiment of the present disclosure, a machine-readable storage medium includes machine-readable instructions for causing a processor to execute a method for use with a medical device to reduce medication errors is provided. The method includes receiving patient-specific information for a patient, and comparing the patient-specific information with a database includes acceptable operating parameters for a medical device. The method also includes providing the modification of operating limit parameters of the medical device for providing a medication to the patient based on the comparison of the patient-specific information with the acceptable operating parameters.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
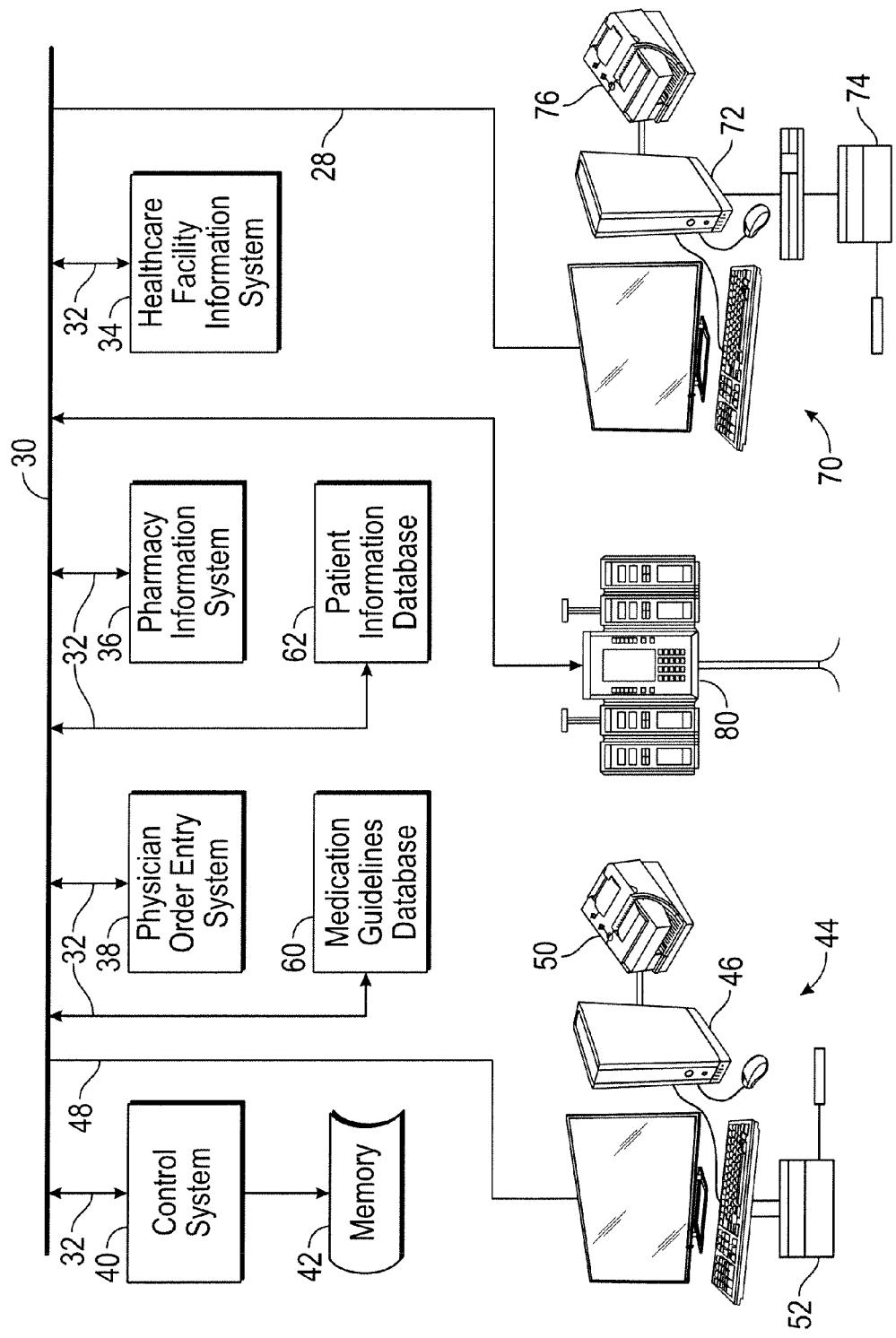
FIG. 1 is a block diagram and graphical representation of a care management system for reducing the possibility of medication errors.

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

The present disclosure provides a system that evaluates patient-specific data, such as a patient's laboratory results or characteristics (e.g., height, weight, gender, body surface area, medical history), in order to determine operating limit parameters (or "dynamic guardrails") for a medical device such as an infusion pump. Incorporating patient-specific laboratory results and other data provides a capability to notify a clinician of scenarios to prevent potential clinical harm. Furthermore, incorporation of a patient's laboratory results and other relevant patient data can assist clinicians in monitoring and intervening in situations related to appropriate methods of intravenous drug administration. The present disclosure also provides for verifying that the right treatment, based on data specific to the right patient, has been given in the right manner, in the right amount, and at the right time.

Several examples will now be presented regarding how the disclosed system can assist clinicians in patient therapy. The disclosed system can, for example, notify a clinician at a medical device that a patient's condition has changed (e.g. change in kidney function and liver function or increasing white blood cell count) and automatically modify (or present modifications to) the parameters, such as maximum and minimum infusion limits, for infusing a medication to the patient based on the changed condition for verification by the clinician. The disclosed system can also, for example, automatically modify infusion parameters if a patient enters a critical situation, such as a changing lab value or other condition. The disclosed system can further, for example, modify the parameters for infusing a medication to a patient if the medication being infused is not associated with an active medication order for the patient. As another example, the disclosed system can modify parameters for infusion of an antibiotic to a patient based on when and how or when the antibiotic was previously infused to the patient. The disclosed system can, for example, modify parameters for infusing an antibiotic if an organism affecting the patient is known to be resistant to the antibiotic. As yet another example, the disclosed system can modify parameters for infusing a medication to a patient if the patient's record indicates the infusion should be discontinued. As another example, when an active order does not exist for a patient associated with a medical device, the disclosed system can send a message to the relevant clinician asking for an order or clarification, such as where a clinician may have given a verbal order that has not been documented or where an infusion may have been ordered to be discontinued but such order was missed.

Referring now to the drawings, FIG. 1 provides an example illustration of an integrated healthcare facility-wide information and care management system 28 in accordance with certain aspects of the present disclosure. Various subsystems of a healthcare facility's information management system are connected together by way of a facility communication system 30. The communication system 30 may include, for example, any one or more of a personal area network (PAN), a local area network (LAN), a campus area network (CAN), a metropolitan area network (MAN), a wide area network (WAN), a broadband network (BBN), the Internet, and the like. Further, the communication system 30 can include, but is not limited to, any one or more of the following network topologies, including a bus network, a star network, a ring network, a mesh network, a star-bus network, tree or hierarchical network, and the like. As shown in FIG. 1, the communication system 30 connects through various interfaces 32 to a healthcare facility information system 34, a pharmacy information system 36, a patient information database 62, a physician order entry system 38, a medication guidelines database 60, and a control system 40 (or "limiting system").

The facility communication system 30 is not meant to be taken in a limited sense. Such a facility communication system 30 may encompass an entire healthcare facility or may be located only in a small area of the healthcare facility. It may also include a communication system in a healthcare facility other than a hospital and may have application to an alternate care facility, such as a patient's home. Additionally, the word caregiver is intended to be used in its broadest sense and is meant to include nurses, physicians, health care specialists, and others who provide care to patients.

The control system 40 in accordance with an aspect of the present disclosure may be, for example, a server or other computer having sufficient memory 42 and processing capability to connect with the communication system 30 and configure a medical device 80. The control system 40 includes operational software or other instructions for carrying out various aspects of the present disclosure, as will be discussed more fully below, enabling communications with other hardware or networks, and data input and output and report generation and printing, among other functions. While the control system 40 is shown as a separate piece of equipment, it will be understood that the control system 40 and the associated memory 42 may also be incorporated into another element, such as the medical device 80.

The communication system 30 may comprise, for example, a wired or wireless Ethernet (IEEE 522.3) utilizing transmitters and receivers positioned throughout the healthcare facility and/or attached to various computers, clinical devices and other equipment used in the facility. In such a wireless system, the signals transmitted and received by the system could be radio frequency (RF), infrared (IR), or other means capable of carrying information in a wireless manner between devices having appropriate transmitters or receivers may be used. It will be immediately understood by those skilled in the art that such a system may be identical to the system set forth in FIG. 1, with the exception that no wires are required to interconnect the various aspects of the system.

In a typical healthcare facility, patient rooms, wards, or areas are typically situated in groups located near a nurse station 44, where the caregivers assigned to care for the patients in the particular area carry out the administrative functions of their duties. Typically, these functions include updating and monitoring the patients' charts, preparation of and administering medication orders, and monitoring and recording any other information deemed necessary by the facility for tracking. There is also usually a room located adjacent the nurse station that is dedicated to storage and/or the preparation of medications to be delivered to patients. This room may contain inventories of commonly used oral, IM, or IV medications. The room may also be used to formulate the contents of infusion bags in accordance with prescribed treatment regimens.

The nurse station 44 will typically include a terminal or computer system 46 connected either directly or through an interface 48 to the communication system 30, allowing users at the nurse station to enter and retrieve patient data or information from other systems, such as the healthcare facility information system 34, the pharmacy information system 36, the physician order entry system 38, or other systems used in the facility. It should be understood that not all users will be provided with access rights to each system. For example, physicians may be able to access the physician order entry system 38 from the nurse station system 44 to enter, edit, or track medication orders, but a caregiver may only be able to view such orders. Moreover, while the present disclosure is described with reference to the computer system 46 being located at a nurse station 44, the computer system 46 may also be a satellite system that is located anywhere in the care-giving facility where it is convenient or efficient to do so. Such a satellite computer system may be operably connected to the communication system 30 using either a wired or wireless network connection. A printer 50 may also be connected to the nurse station computer system 46 for printing reports, bar codes, labels, or other materials, and a bar code reader 52 may be provided for reading bar codes on medication labels, reports, or other items having bar coded labels provided for identification.

In a different embodiment where radio frequency identification (RFID) tags are used with medications, patients, equipment, or in other ways, the nurse station 44 may also include an interrogator or RFID reader (not shown) for use with the RFID tags.

In accordance with aspects of the present disclosure, a medication database carrier (MDC) or medication guidelines database 60 stores information that is provided to monitor medication parameters or other information used by a caregiver to program a medication administration device 80 to deliver medication to a patient. Various types of information may be stored in the memory of the medications guidelines database 60, including data bases containing information about drug interactions and possible contraindications and/or side-effects of medications, and established guidelines for the administration of various medications. For example, the guidelines may include institutionally-established guidelines or limits on drug administration parameters, such as dosage, frequency of administration, and other delivery related information such as, for example, appropriate flow rates and infusion durations for programming infusion pumps. Additionally, the guidelines may encompass guidelines for providing drug administration appropriate to a particular patient or to treatment areas having different sets of delivery parameters for similar medications, such as medication administration directed to geriatric, pediatric, and oncology patients. Guidelines may also be included that are directed to particular therapy regimens, such as chemotherapy regimens or regimens for treating chronic infection or pain. The term database as used herein will be understood by those skilled in the art to be used as is commonly understood. That is, the term database refers to a collection of values or information organized, formatted, and stored in such a manner as to be capable of being retrieved and analyzed using an appropriate program contained in software or other form.

In one embodiment of the present disclosure, the medications guidelines database 60 may be interfaced to the nurse station computer system 46 or any other of the information systems of the central system of an institution through a cradle or other docking device that provides a connection between the medications guidelines database 60 and the computer system 46. In this embodiment, use of the cradle allows information to flow between the medications guidelines database 60 and the nurse computer system 46. This information may then be processed and stored on the computer system 46, or the information may be communicated by the computer system 46 through the interface 48 to various other facility information systems over the communication system 30. In this manner, information from the pharmacy information system 30, for example, may be communicated through the communication system 30, the nurse station 44 computer system 46, and to the medications guidelines database 60. Similarly, information contained within the medications guidelines database 60 may be communicated through the nurse station computer system 46, the interface 48, and the communication system 30 to any of the interconnected systems 34, 36, 38, 40, or 62.

The medications guidelines database 60 may be stored on a device, such as a server. The healthcare facility may also or alternatively have the medication guidelines database 60 centrally located in the memory 42 of the control system 40. The medication guidelines database 60 includes medication information and/or databases or libraries, including institutionally generated guidelines for the delivery of medication to a patient, as well as drug interaction information or information concerning possible drug side-effects, and that is portable such that it can be carried by a caregiver to and from a patient's bedside. The medications guidelines database 60 may also have a storage capability and technology for interfacing with a computer system or network so that information may be communicated between the medications guidelines database 60 and other devices, such as computers, medication administration devices, clinical devices such as vital signs monitoring devices and the like.

A general concept embodied in the medications guidelines database 60 is to provide medication administration parameters or other information that may be entered into a medication administration device 80, such as an infusion pump In accordance with aspects of the present disclosure, the control system 40 is configured to obtain patient-specific information from the patient information database 62, medication information from the medication guidelines database 60, and device information from the medical device 80. The patient information database 62 may itself obtain and store patient-specific information retrieved from the physician order entry system 38, the pharmacy information system 36, and the healthcare facility information system 34. In certain aspects, information may be retrieved information from the medical device 80 prior to actual medication administration, and the control system 40 can evaluate the medication information from the medication guidelines database 60 in view of the patient-specific information for the patient associated with the medical device 80 to determine if parameters entered into the medical device 60 fall within institutionally established guidelines for the administration of a particular medication. If the comparison indicates that the parameters or information entered into the medication administration device are appropriate in that they fall within the established guidelines, then an indication to that effect may be provided to the caregiver and the caregiver may then begin medication administration.

Alternatively, if the comparison indicates that one or more parameters or information do not meet the established guidelines, a warning or alert may be provided to the caregiver that one or more parameters or a portion of information has been incorrectly entered into the medication administration device, and that corrective action or an override is required before medication administration can begin. In another embodiment, the medication administration device may be automatically inhibited from starting administration of a medication unless it receives a signal from the control system 40 that the comparison was favorable, thus providing a fail-safe against incorrect administration of the medication.

For example, a patient's laboratory testing results indicate the patient has reduced renal function. The prescribed medication for the patient, however, will further reduce renal function in any patient, which, if the patient were to have normal renal function, would still fall within institutionally established guidelines as defined by the medication guidelines database 60. This specific patient, however, has reduced renal function. Based on the identification of specific information of the patient regarding the patient's reduced renal function, the control system 40 will display an alert at the medical device 80 for providing the prescribed medication, and optionally restrict a caregiver from administering the prescribed medication using the medical device 80.

In certain aspects, information may be retrieved information from the medical device 80 after actual medication administration begins, and the control system 40 can evaluate the medication information from the medication guidelines database 60 in view of the patient-specific information for the patient associated with the medical device 80 to determine if the parameters currently being used by the medical device 60 fall within institutionally established guidelines for the administration of a particular medication. For instance, the evaluation for a medication being administered may occur during administration of the medication, such as when doses are adjusted, for example, to maintain blood pressure or heart rate or blood sugar levels. Errors may then be prevented and advisories posted at any point during the medication administration, which may be over 10 minutes, 10 hours, or even 10 days.

Institutionally established guidelines or more widely accepted protocols for the administration of medications stored in the medication guidelines database 60 include, for example, medication administration parameters or other information, such as bolus size, maximum dose per hour, maximum continuous dose, volume to be infused, flow rate, and maximum concentration. The medication guidelines database 60 may have preestablished values for infusion parameters that have been generated by the healthcare facility or adopted by the facility. They may comprise the considered "best practices" of the facility and may be updated from time to time. These preestablished values may contain "hard" and "soft" limit values or dynamic guardrails on dosing parameters and other infusion parameters. The facility may set a soft limit for a drug infusion parameter that is a value not normally exceeded in the administration of this drug, but which may be exceeded in exceptional circumstances. The facility may set a hard limit on a drug infusion parameter that is a value not to be exceeded in this facility. Similarly, the facility may set a soft limit value for a drug infusion parameter for doses that are below a normal range used by the facility, and a hard limit on a drug infusion parameter that is a value below which a dose may not be given in the facility. In such circumstances, a low or high dose alert may be triggered to prevent potential underdosing or overdosing.

Once the infusion parameter values have been entered into the medical device 80 by the caregiver and those values have been communicated to the control system 40, the control system 40 may then enter a verification stage in which it compares each of the selected values against the medication guidelines database 60 and patient-specific information from the patient information database 62 to verify that the entered infusion values are within acceptable ranges. If a value contravenes a hard limit, the control system 40 may generate an alarm at the control system 40 or the medical device 80 and require a value change before operation of the medical device 80 can begin. If the selected infusion parameter value contravenes a soft limit, the control system 40 may require an acknowledgment from the caregiver that he or she understands that the value entered is outside a soft limit and that this value is nevertheless to remain in force before the medication administration can begin. In certain aspects, the control system 40 may also require that the caregiver provide a reason for entering the value. If the acknowledgment is obtained from the caregiver, the control system 40 may authorize the administration of the medication by the medical device 80.

The control system 40 is capable of retrieving medication administration parameters or information from a medication administration device 80, and storing data or information concerning various transactions in its memory 42 representing the identity and treatment regimens for medications given to a patient, as well as other information, such as caregiver identity, equipment location, patient vital signs information, or any other information sought to be recorded. The control system 40 may also store data or information concerning primary or secondary validation of previous and/or duplicate transactions of medical treatment information. The control system 40 may also provide, for display, messages or other information to a caregiver, such as warnings or prompts to enter data, related to medication administration. Moreover, information entry means of the control system 40 may be used for manually entering information into the control system 40 for storage in the memory 42 of the control system 40. In certain aspects, the control system 40 may store information in memory 42 representing patient specific treatments spanning multiple treatments or hospitalizations. For example, the control system 40 may identify and track how much chemotherapy a patient receives in order to prevent a maximum dosage of chemotherapy over a time period being exceeded. As another example, the control system 40 may identify and track how much alcohol is contained in a medication being provided to the patient in order to prevent a certain amount of alcohol being exceeded for a patient having liver failure.

While specific examples of a control system 40 are set forth herein, it will be understood that the control system 40 is meant to include any device that carries out the basic concept of the disclosure. That is, a device that receives medication administration or treatment information from a medication administration device, such as, for example, but not limited to, an infusion pump or other instrument which performs similar functions, receives information specific to one or many patients, and has a processor capable of comparing the received information to institutionally established medication administration guidelines or other pertinent information or data, such as drug interaction information and/or a library of possible side-effects, and then providing an indication of the result of the comparison to a caregiver before administration of a medication to a patient is begun, will accomplish the aims of the present disclosure. A particularly advantageous embodiment includes storing information about the medication administration, such as the medication administration or treatment parameters, and/or other information, such as the identity of the patient and caregiver, in the memory of the medications guidelines database 60 until the medications guidelines database 60 re-establishes a communication connection with the control system 40, whereby the information stored in the memory of the medications guidelines database 60 may be communicated to the control system 40 and incorporated into one or more of an institution's information databases. Similarly, information about the medication administration, such as the medication administration or treatment parameters, and/or other information, such as the identity of the patient and caregiver, may be stored in the memory of the medical device 80 until, for example, the medical device 80 re-establishes a communication connection with the control system 40. Updating the databases provides a verification that the treatment has been rendered, thereby avoiding a duplicate treatment. In this manner, the present disclosure "closes the loop" ensuring that the right medication has been given in the right manner to the right patient through the rights route at the right time.

It is not unusual at present to find patient stations 70 having a computer 72 located at patient bedsides in a healthcare facility. Such stations 70 may serve a single patient, or may serve more than one patient, depending on the design and arrangement of the patient area. There may also be a variety of equipment or clinical devices attached to the bedside computer 72. Examples of such devices are a bar code reader 74, a printer 76, patient monitoring equipment (not shown) for monitoring patient vital signs, or other patient-specific assets (e.g., medical devices) assigned to the patient. Other infusion or drug delivery devices and/or patient monitoring equipment such as cardiac or respiratory monitors may also comprise or form a part of the medical device.

The bedside equipment and clinical devices are typically equipped with data communication technology such as RS 232 serial ports or proprietary communication ports that allow information and data to be communicated to and from the equipment or clinical device. Using this communication technology, the bedside equipment and clinical devices may be connected to the bedside computer 72, or, alternatively, they may be connected, either by wire or wireless system, to the facility communication system 30. Wireless technology, such as RF, infrared (IR), or other wireless communication protocols, may be used, and wired technology establishing a local area network (LAN), Ethernet, or others may be used.

In accordance with an aspect of the present disclosure, the medical device 80 may include a communication device 82 used to provide communications between the medical device and the control system 40. Various forms of such a communication device may be used, such as wired or wireless communication.

One particular mode of operation of the present disclosure will now be described. A patient entering a healthcare facility is provided with a wrist band, necklace, ankle band, or other band, chain, or device designed to remain affixed to or embedded in the patient during the patient's entire stay in the healthcare facility (the "patient ID"). The patient ID is designed to remain affixed in a manner so that the patient can be identified even if unconscious or otherwise unresponsive. The patient ID is used to identify specific patient data, such as the patient's name and other information that the facility has determined is important, such as age, allergies, or other vital information. The patient identifying device may comprise a bar code, written information, or an electronic information storage device, such as an RF transponder (e.g., RFID tag), that contains the information, or other device affixed to the patient. In the case where the patient-specification information may also include the patient's medication administration record (MAR). This would allow for consistent documentation and also checks against drug interaction in the medication guidelines database 60.

Such RFID tags, barcodes, and other technologies useful in identification, may be applied to others and to other things in providing healthcare to patients. For example, physicians, nurses, and other caregivers, as well as others who have access to patients and facilities, may also have an RFID tag that can be read anywhere in the healthcare facility. The medical fluid containers may contain RFID tags having information about the contents of the container as well as the patient for whom they have been prepared, the pharmacist who prepared them, and the physician who prescribed them. The infusion pumps and other healthcare instruments and devices may have RFID tags useful for inventory control. Even though the instruments may be connected to the healthcare facility communication system 30, RFID tags can be useful for manual inventory purposes as well as for other purposes. Their low cost make them attractive as a backup support system.

After the patient is admitted and situated in a bed within the facility, the patient is typically evaluated by a physician and a course of treatment is prescribed. The physician prescribes a course of treatment by preparing an order that may request a series of laboratory tests or the administration of a particular medication to the patient. In some case, the physician prepares the order by filling in a form or writing the order on a slip of paper to be entered into the healthcare facility system for providing care. In other cases, the physician may enter the medication order directly into a physician order entry system 38 (FIG. 1) or may instruct a nurse or other care-giving professional to do so. In yet another case, the physician may use the Internet to forward and enter a prescription for the patient into the pharmacy system.

Depending on the arrangement at the healthcare facility, the physician's order or prescription may directly reach a website for the pharmacy information system 36 or may go to a website for the healthcare facility where it may then be routed to the pharmacy information system 36.

Pharmacy information systems 36 may enable a safer physician medication order process. The pharmacy information system 36 may provide the physician with a list of available drugs from which the physician may select. The pharmacy information system 36 may contain a drug library having the list of available drugs but may also contain and present to the physician the drug names associated with recommended dosages and dose limits that have been established or adopted by the healthcare facility. In such a case where the physician need only select items from the computer screen rather than having to manually type in drug names and drug administration numbers (such as infusion rates, times, etc.) associated with administration of the medication, a more accurate medication process should result.

If the order is for administration of a particular medication regimen, the order will be transmitted to the facility's pharmacy information system 36. The pharmacy reviews the order and prepares the medication according to the requirements of the physician. Typically, the pharmacy packages the medication in a container, and a copy of the order, or at a minimum the patient's name, the drug name, and the appropriate treatment parameters are represented on a label or other device that is affixed to the drug container. This information may be represented by a bar code, or it may be stored in a smart label, such as a label having an embedded computer, or in a passive device such as an RFID tag discussed above.

Once the order has been prepared, the order is sent to the nurse station 44 for matching with the appropriate patient. Alternatively, if the medication is for a commonly or routinely prescribed medication, the medication may be included in an inventory of medications that is stored in a secure cabinet adjacent the nurse station 44. In such a case, the nurse station 44 will receive a list of orders from the pharmacy information system 36 that may be drawn from the inventory adjacent the nurse station 44. The caregiver will enter a unique identifier at the cabinet to gain access in accordance with standard practice. The caregiver or other professional assigned the task of gathering medications will then match the orders received from the pharmacy information system 60 to the medications stored in the inventory and pull those medications that are to be delivered to specific patients. These procedures are carried out whether the medication to be delivered is an oral medication, or a medication that is to be delivered intramuscularly or through an infusion.

When the prescribed time for delivery of the medication or medications arrives, the medications are carried to the patient's area and administered to the patient by the caregiver. In the case of drugs to be delivered via infusion, the caregiver hangs the infusion bag and prepares the infusion line, attaches the bag to an infusion pump 80, and sets up the infusion pump to deliver the medication by programming the pump with values for various parameters that are used by the pump to control delivery of the medication to the patient. When the medication delivery parameters are entered into the pump, the pump communicates the entered parameters to the medications guidelines database 60 where the parameters are compared by the control system 40 to institutionally established medication administration guidelines stored in the medication guidelines database 60 in view of patient-specific information from the patient information database 62. If the outcome of the comparison indicates that the entered parameters are within the guidelines, a message is provided to the caregiver informing the caregiver that the entered parameters are acceptable and that delivery of the medication may begin.

Alternatively, the infusion pump may include a fail-safe circuit or device that prohibits initiation of infusion until the medical device 80 receives a signal from the medications guidelines database 60 that the entered parameters are within the institutionally established or approved guidelines. Once such a signal is received by the infusion pump, the pump may be started to deliver the medication. Where the comparison is not favorable, such as where one or more parameters fall outside of the institutionally established or approved guidelines, a message to that effect is provided to the caregiver, and the caregiver is prompted to correct the out-of-range parameter or parameters, or enter an override. It will be understood by those skilled in the art that these procedures may be embodied in a portable medications guidelines database 60 such as a PDA as described above, or they may be embodied in an MDC that is integrated in or associated with a particular medical device.

Figure 2:
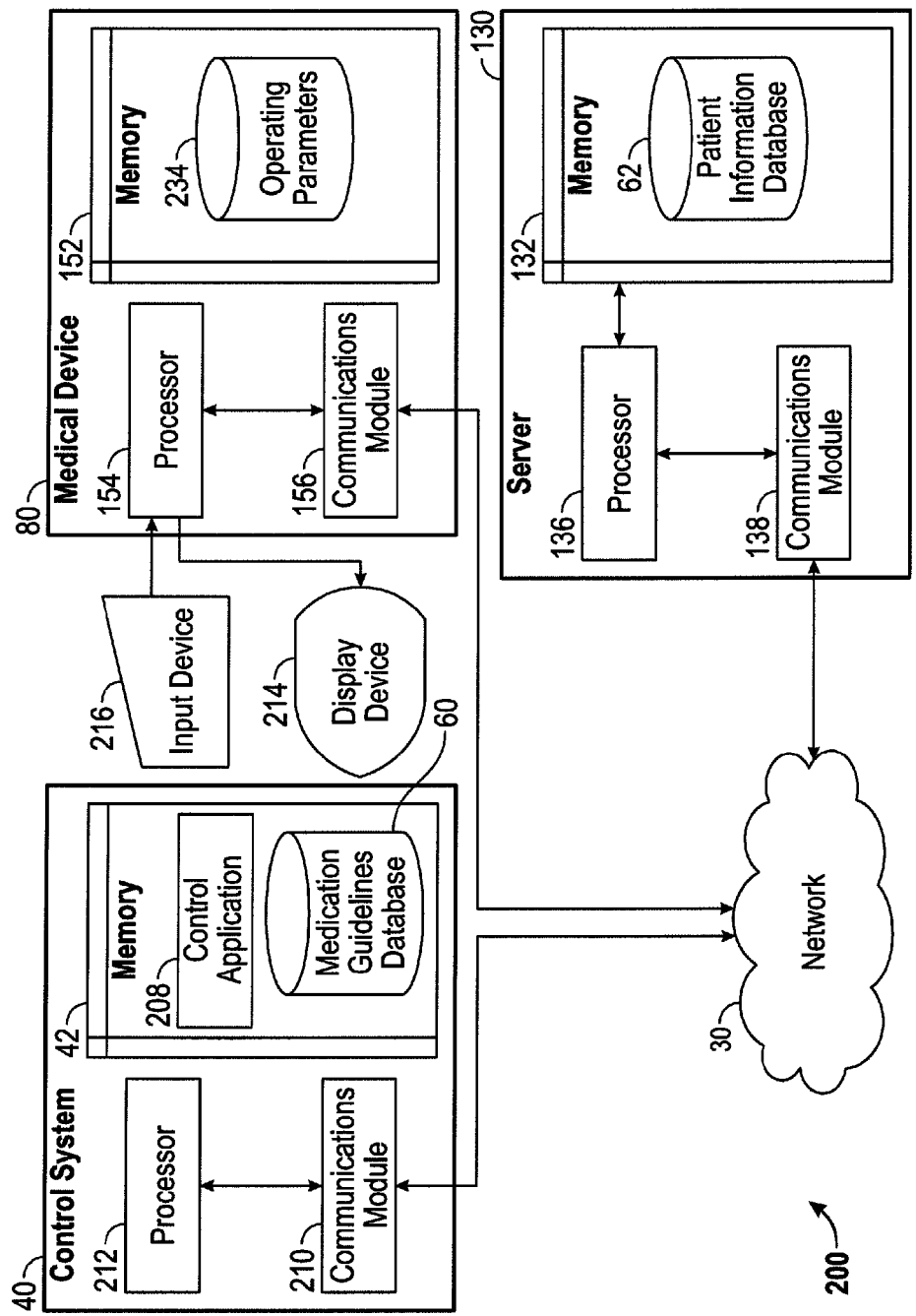
FIG. 2 is a block diagram illustrating an example control system, server, and medical device from the architecture of FIG. 1 according to certain aspects of the disclosure.

FIG. 2 is a block diagram 200 illustrating an example control system 40 (or "limiting system"), medical device 80, and server 130 from the architecture of FIG. 1 according to certain aspects of the disclosure. The control system 40, the medical device 80, and the server 130 are connected over the network 30 via respective communications modules 210, 156, and 138. The communications modules 210, 156, and 138 are configured to interface with the network 30 to send and receive information, such as data, requests, responses, and commands to other devices on the network. The communications modules 210, 156, and 138 can be, for example, modems or Ethernet cards and communicate over a wired or wireless connection.

The control system 40 includes a processor 212, the communications module 210, and a memory 42 that includes a control application 208 and a medication guidelines database 60. The medication guidelines database includes acceptable operating parameters for providing medication to a patient using the medical device 80. In certain aspects, the acceptable operating parameters of the medication guidelines database 60 include a plurality of rules indicating whether the patient-specific information includes a value (e.g., physiological data reading) that is within or exceeds a threshold define by at least one of the rules. The rule can indicate, for example, a maximum or minimum total amount of the medication to provide to the patient over a period of time. For example, if a medication is provided solely based on an obese patient's weight, then the amount of the medication given over a one hour period may significantly exceed known safety limits. Accordingly, a limit may be placed on delivery of the medication based on a total amount of medication delivered (as non-weight based) or the total amount delivered over a period of time where the medication was programmed by the user as a weight based delivery. This addresses the patent of increased safety during medication delivery when programming an infusion as weight based medication and the limits for that medication are established within the hospital dataset as both 1) weight based limits and 2) non-weight based (not-to-exceed) limits. As such, the acceptable operating limit parameters in the medication guidelines database 60 can be hard or soft limits/guardrails. The acceptable operating limit parameters in the medication guidelines database 60 can include a rate at which to provide the medication, an amount of the medication to provide, and a length of time to provide the medication.

The medical device 80 is configurable with operating limit parameters for providing medication to a patient. The medical device 80 can be, for example, an infusion pump or ventilator. The medical device 80 includes an input device 216, such as a keypad, for manual entry of operating parameters 234 (e.g., dosing limits), as well as a display device 214, such as a monitor, for notifications and confirmation of entered operating parameters 234.

The processor 212 of the control system 40 is configured to execute instructions, such as instructions physically coded into the processor 212, instructions received from software in memory 42, or a combination of both. For example, the processor 212 of the control system 40 executes instructions to receive patient-specific information for a patient from a patient information database 62 stored in a memory 132 of a server 130. The patient-specific information can be received from an external data system (e.g., server 130) in a native message format of the external data system, and the processor 212 of the control system 40 can be configured to convert the patient-specific information into an internal messaging format configured for use with the control system 40. The processor 212 can be configured to perform the conversion according to the system and method of converting messages being sent between data systems using different communication protocols and message structures described in U.S. patent application Ser. No. 13/421,776, entitled "Scalable Communication System," and filed on Mar. 15, 2012, the disclosure of which is hereby incorporated by reference in its entirety for all purposes. The memory 42 of the control system 40 can include, for example, an interface module for communicating with the server 130. The interface module can include information on the communication protocol and data structure used by the server 130 and is configured to both receive messages from and transmit messages to the server 130.

The processor 136 of the server 130 is configured to collect and store in the patient information database 62 patient-specific information from the physician order entry system 38, pharmacy information system 36, and healthcare facility information system 34 over the network 30. In certain aspects, the patient information database 62 can be stored in the memory 42 of the control system 40. The patient-specific information includes, for example, laboratory data for a patient. The laboratory data can include a blood coagulation measure, a vitamin level, a platelet count value, a thromboplastin time, or a serum level for a patient. The patient-specific information can also include a medication ordered for the patient, a time at which the medication is ordered for the patient, a treatment plan for the patient, a medication resistance of the patient, a weight of the patient, a height of the patient, a body surface area of the patient, an age of the patient, a gender of the patient, or an ethnicity of the patient.

The processor 212 of the control system 40 is configured to compare the acceptable operating parameters in the medication guidelines database 60 with the patient-specific information from the patient information database 62, and provide a modification (e.g., by instructing a processor 143 of the medical device 80) the operating parameters 234 in the memory 234 of the medical device 80 for providing the medication to the patient based on the comparison of the acceptable operating parameters with the patient-specific information. The modified operating parameters 234 can be provided for display on the display device 214 of the medical device 80, or can automatically be implemented in the operating parameters 234 of the medical device 80.

The processor 212 can, for example, modify the operating parameters 234 based on the patient-specific information by defining at least one of a maximum value or minimum value for at least one operating parameter 234 associated with delivery of the medication to the patient based on the patient-specific information. The processor 212 can, for example, modify the operating parameters 234 based on the patient-specific information by defining at least one of a pair of a soft maximum value that can be exceeded and a hard maximum value that cannot be exceeded, or a soft minimum value that can be exceeded and a hard minimum value that cannot be exceeded for at least one operating parameter 234 associated with delivery of the medication to the patient based on the patient-specific information from the patient information database 62.

Several examples of modifications made by the control system 40 to the operating parameters 234 of the medical device 80 based on patient-specific information and the medication guidelines database 60 will now be presented. In one example, if information specific to a patient indicates the patient has two consecutive blood sugar results greater than 180 mg/dL within a 24 hour period, then the operating parameters 234 of the medical device 80 providing medication to the patient can be modified by the control system 40 to reflect the patient suffering from hyperglycemia. As a further example, if information specific to a patient indicates the patient has a blood sugar result of less than 70 mg/dL, then the operating parameters 234 of the medical device 80 providing medication to the patient can be modified by the control system 40 to reflect the patient suffering from hypoglycemia (e.g., to decrease an amount of insulin being provided to the patient). As yet another example, if information specific to a patient indicates the patient has a serum potassium result of less than or equal to 3.2, then the operating parameters 234 of the medical device 80 providing medication to the patient can be modified by the control system 40 to reflect the patient suffering from hypokalemia, and optionally recommending an increase an amount of potassium being provided to the patient. As another example, if information specific to a patient indicates the patient has a serum potassium result of less than or equal to 3.5 while on digoxin or dofetilide, then the operating parameters 234 of the medical device 80 providing medication to the patient can be modified by the control system 40 to reflect the patient suffering from hypokalemia while taking medications. As a further example, if information specific to a patient indicates the patient has a serum potassium result of greater than or equal to 5.0 while on angiotensin converting enzyme inhibitors, angiotensin receptor II blockers, potassium sparing diuretics, potassium supplements, or aliskiren, then the operating parameters 234 of the medical device 80 providing medication to the patient can be modified by the control system 40 to reflect the patient suffering from hyperkalemia while taking medications. As another example, if information specific to a patient indicates the patient has a serum calcium result of less than 8.6 mg/dL, then the operating parameters 234 of the medical device 80 providing medication to the patient can be modified by the control system 40 to reflect the patient suffering from hypocalcemia. As yet another example, if information specific to a patient indicates the patient has a serum calcium result of greater than 10.2 mg/dL, then the operating parameters 234 of the medical device 80 providing medication to the patient can be modified by the control system 40 to reflect the patient suffering from hypercalcemia. As a further example, if information specific to a patient indicates the patient has a serum magnesium result of less than 1.5 mg/dL, then the operating parameters 234 of the medical device 80 providing medication to the patient can be modified by the control system 40 to reflect the patient suffering from hypomagnesemia.

As another example, if information specific to a patient indicates the patient has a serum magnesium result of more than 2.4 mg/dL, then the operating parameters 234 of the medical device 80 providing medication to the patient can be modified by the control system 40 to reflect the patient suffering from hypermagnesemia. As yet another example, if information specific to a patient indicates the patient has a serum phosphate result of less than 2.7 mg/dL, then the operating parameters 234 of the medical device 80 providing medication to the patient can be modified by the control system 40 to reflect the patient suffering from hypophosphatemia. As a further example, if information specific to a patient indicates the patient has a serum phosphate result of more 4.5 mg/dL, then the operating parameters 234 of the medical device 80 providing medication to the patient can be modified by the control system 40 to reflect the patient suffering from hyperphosphatemia. As another example, if information specific to a patient indicates the patient has a serum magnesium or serum phosphorus concentration above a threshold value (e.g., set by a user), then the operating parameters 234 of the medical device 80 providing medication to the patient can be modified by the control system 40 to reflect the patient suffering from high or low magnesium or high or low phosphorus.

In one example, if information specific to a patient indicates the patient has a blood coagulation measure or "INR" greater than 3.0, and Vitamin K has been ordered for the patient within 24 hours of the INR collected date and time, then the operating parameters 234 of the medical device 80 providing medication to the patient can be modified by the control system 40 to reflect high INR and Vitamin K for the patient. As another example, if information specific to a patient indicates the patient has an INR greater than 3.5 within 72 hours of an order of Warfarin for the patient, then the operating parameters 234 of the medical device 80 providing medication to the patient can be modified by the control system 40 to reflect high INR and Warfarin for the patient. As another example, if information specific to a patient indicates the patient has platelet count less than 125,000/L, or that the patient's platelet count has fallen by more than 50% while on (or within 14 hours after a discontinuation of) a certain medication, such as unfractioned heparin, dalteparin, enoxaparin, tinzaparin, or glycoprotein inhibitors, then the operating parameters 234 of the medical device 80 providing medication to the patient can be modified by the control system 40 to reflect the patient suffering from thrombocytopenia and a critical drop in a drug. As another example, if information specific to a patient indicates the patient has not had a baseline platelet count within seven days prior to the start of a scheduled dose of heparin, then the operating parameters 234 of the medical device 80 providing medication to the patient can be modified by the control system 40 to reflect not having a baseline platelet prior to starting heparin. As another example, if information specific to a patient indicates the patient has not had a platelet count performed within a certain number of hours once heparin has been active for four days, then the operating parameters 234 of the medical device 80 providing medication to the patient can be modified by the control system 40 to reflect no platelet count within the certain number of hours and having taken heparin for four days.

In certain aspects where the medical device 80 is configurable with operating parameters 234 for providing a mixture comprising at least two medications to a patient, the medication guidelines database 60 includes acceptable operating parameters for providing the mixture to the patient using the medical device. For example, if an anesthetic agent (e.g., Bupivacaine) is mixed with an analgesic agent (Fentanyl) in a single solution drug mixture cocktail, then the medication guidelines database 60 can evaluate the concentration of the two agents and determine limits for dosing the drug mixture cocktail based on the concentration of the two agents in the drug mixture cocktail.

In certain aspects, the processor 212 of the control system 50 being configured to compare the acceptable operating parameters from the medication guidelines database 60 with the patient-specific information from the patient information database 62 includes the processor comparing a first weight (e.g., lean body weight or total body weight) of the patient provided to the medical device 80 with a second weight (e.g., lean body weight or total body weight) of the patient provided to another medical device. For example, on a first channel, a patient's weight is based on lean body weight as 70 kilograms. On a second channel, the patient's weight is based on a total body weight of 80 kilograms. In other words, the control system 50 permits two medical devices 80 to accept different weights of a patient for different medications. The system would further allow the institution to establish an allowable percent or absolute value of variance between weights used on the same patient. For example if the allowed variance is 10%, then all weights in the system would have to be within 10% of one another. This would prevent patient weight entry errors that can result in serious over or under dosing. This is covered in Paragraph 0063 as well. Such functionality is particularly relevant for very obese patients that may have a significant difference in their lean body weight and their total body weight. Dosing a very obese patient that is based on total body weight can be inappropriate.

As such, the control system 40 is configured to place guardrails based on a patient's weight. Specifically, the control system 40 is configured to identify and compare the weight that is entered on the first channel and the second channel. For example, if an infusion is running on a pediatric patient of 10 kilograms on a first channel and when a second channel is being prepared a default weight of 10 kilograms is entered based on the first channel. The clinician accidentally enters "110" kilograms as the weight of the pediatric patient on the second channel, which may cause the pediatric patient to receive about ten times the amount of the drug they would be prescribed simply because of the clinician's error. The control system 40 can indicate, for example, that the patient's weight being entered is out or differs by a certain percentage (e.g., 10%, 20%) or by an absolute value, e.g., 5 pounds or kilograms set by a user or institution, and apply either hard or soft limits to the medication being provided to the patient.

In certain aspects, the processor 212 of the control system 50 being configured to modify the operating parameters 234 of the medical device 80 for providing the medication to the patient includes the processor 212 being configured to modify the operating parameters 234 based on a determination of the acceptable operating parameters for a person having the patient's body surface area (e.g., determined using information from the patient information database 62). Body surface area or actual surface area of the patient can be a more accurate measure for dose modification by the control system 40 for determining the operating parameters 234 as compared to a patient's weight. In certain cases, a better therapeutic response can be obtained for a medication if the medication is dosed based on a patient's body surface area as opposed to the patient's weight. For example a lean patient weighing 350 lbs will have less body surface area than an obese patient weighing 350 lbs. If body surface area were not considered, then both patients would be given the same dose of a medication, which can be incorrect. If a medication is provided to a patient based on the patient's weight, but the body surface area indicates that the patient is being provided too much of the medication as determined by the control system 40, then the control system 40 can modify the operating parameters 234 accordingly.

Similarly, in certain aspects, the processor 212 of the control system 50 being configured to modify the operating parameters 234 of the medical device 80 for providing the medication to the patient includes the processor 212 being configured to modify the operating parameters 234 based on a determination of the acceptable operating parameters for a person's weight. Patient weight can be an accurate measure for dose modification by the control system 40 for determining the operating parameters. In certain cases, a safer therapeutic response can be obtained for a medication if the medication does not exceed the maximum total dose (e.g., "not-to-exceed") that is dosed based not a patient's weight when the dose was programmed as a weight-based dose. For example if the medication was ordered by the physician and the dose was based on the patients weight and the maximum total dose (not-to-exceed) non-weight based limit was exceed an alert will be displayed to the user telling them the weight based dose programmed exceeds the hospital established database maximum (not-to-exceed) non-weight based limit. 350)

In certain aspects, the processor 212 of the control system 40 is configured to provide a notification to the medical device 80 indicating that the operating parameters 234 for providing the medication to the patient have been modified based on the patient-specific information from the patient information database 62. For example, the processor 212 of the control system 40 can instruct the processor 154 of the medical device 80 to display an alert with operating parameters 234 that have been modified by the control system 40 based on patient-specific information and the medication guidelines database 60. The display can be seen by a clinician near the medical device 80. In certain aspects, the processor 212 is further configured to receive an input from a caregiver to override the modification of the operating parameters 234. Thus, the caregiver can override the modification provided by the control system 40 by using the input device 216 of the medical device 80. In addition to a confirmation to override the modified operating parameters, the caregiver can also be required to provide a reason why the caregiver has overrode the modification of the operating parameters 234. The processor is configured to record when the caregiver overrides the modification of the operating parameters 234, such as in the memory 42 of the control system 40.

In certain aspects where the processor 212 of the control system 40 is configured to provide a notification to the medical device 80, the processor 212 is configured to receive configuration parameters for determining whether to provide the notification based on an identity of a caregiver, identification of a location of the medical device, or an institutional preference. For example, the processor 212 can configure the medical device 80 to require a confirmation step for operating parameters 234 that exceed high limit warnings (e.g., a maximum amount for a medication dose), but not for low limit warnings (e.g., a minimum amount for the medication dose). As another example, the processor 212 can configure the medical device 80 to require a confirmation step for certain critical medications, or for a first time a medication is provided to a patient using the medical device 80. The configuration for when to display an alert and for what reasons can be set by an institution in which the medical device 80 is located.

As yet another example, the processor 212 can configure the medical device 80 to display alerts and/or require a confirmation step based on a care area in which the medical device 80 is located or by the caregiver associated with the medical device. For instance, in an operating room, the operating parameters 234 for providing a medication are usually very different than the operating parameters 234 for providing a medication to a patient in a pediatric ward. The operating parameters 234 of the medical device 80 can be configured or otherwise modified by the control system 40 accordingly. As another example, if a caregiver associated with a medical device 80 is highly trained with over 10 years of experience, then an alert may not be displayed to the caregiver as compared to another caregiver with limited experience.

Figure 3:
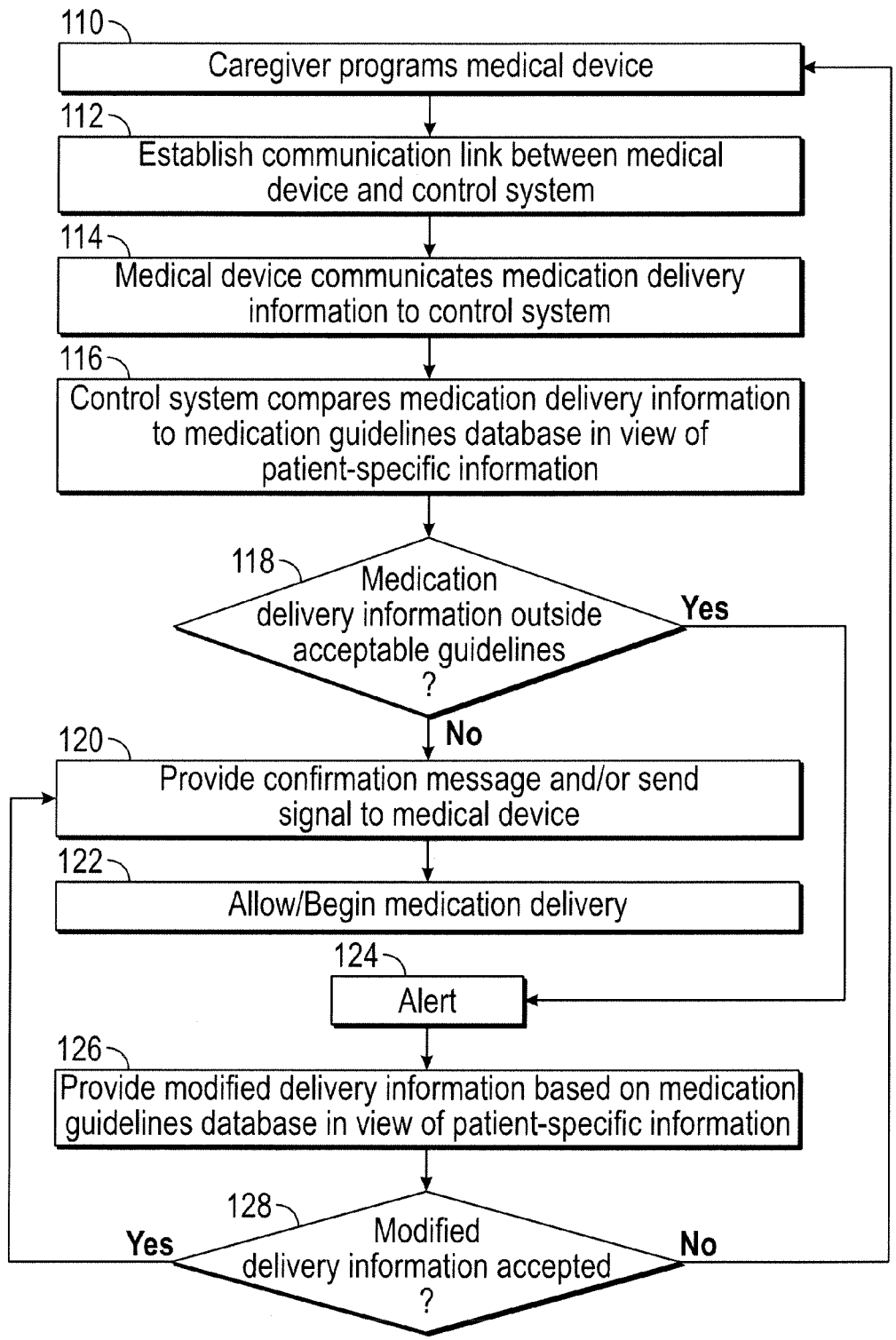
FIG. 3 is functional block diagram illustrating an example process for reducing medication errors for a patient using a programmable medical device, such as an infusion pump, and a control system, by referencing a guidelines database in view of information specific to the patient.

FIG. 3 is functional block diagram illustrating an example process for reducing medication errors for a patient using a programmable medical device 80 and a control system 40 by referencing a medication guidelines database 60 in view of information specific to the patient. Beginning in step 110, a caregiver programs a medical device 80 with operating parameters 234 or other information necessary to deliver a particular medication to a patient. Next, in step 112, a communication link between the medical device 80 and the medications guidelines database 60 is established. In certain aspects, the communication link between the medical device 80 and the medications guidelines database 60 is established prior to the caregiver programming the medical device 80, where for example the medical device 80 may initially be programmed (e.g., for caregiver review and approval) by another system. The medical device 80 communicates the operating parameters 234 or other information to the control system 40 in step 114. The processor 212 of the control system 40 then compares the communicated operating parameters 234 of the medical device 80 to institutionally established guidelines in the medication guidelines database 60 in view of patient-specific information for the patient received from the patient information database 62 of the server 130. In decision step 118, a determination is made whether any of the operating parameters 234 of the medical device 80 are out of range, that is, fall outside of the institutionally established guidelines or limits of the medication guidelines database 60 in view of the patient-specific information.

If it is determined that the operating parameters 234 of the medical device 80 are within range in view of the patient-specific information, then the process proceeds to step 120 in which a confirmation message for the operating parameters 234 is sent to the medical device 80. Upon receipt of this confirmation message, the medical device 80 unlocks and allows initiation of the medication delivery by the medical device 80. This approach would have particular application to the hard and soft limits feature in the drug library, as discussed above. Should a soft limit be contravened, an input to the medical device 80 from the caregiver would be required before the control system 40 unlocks the medical device 80. Should a hard limit be contravened, the medical device 80 would not be unlocked by the control system 40. Next, in step 122, medication delivery by the medical device 80 is permitted to proceed.

If it is determined that any of the operating parameters 234 of the medical device 80 are out of range in view of the patient-specific information, then an alert is provided to the medical device 80 in step 124. The alert can be audible, visible, or both. For example, messages such as "consistent" or "not inconsistent" may be provided thus giving the caregiver further information upon which to base her decision as to using the medical device 80. These latter messages may indicate that the parameters are "consistent" with the healthcare facility guidelines stored in the control system 40. Next, in step 126, modified operating parameters 234 determined by the control system 40 based on the medication guidelines database 60 in view of the patient specific information from the patient information database 62 are provided to the medical device 80. If the modified operating parameters 234 are accepted in decision step 128, the process proceeds to step 120 described above. If the modified operating parameters 234 are not accepted in decision step 128, the process proceeds to beginning step 110 described above.

Figure 4:
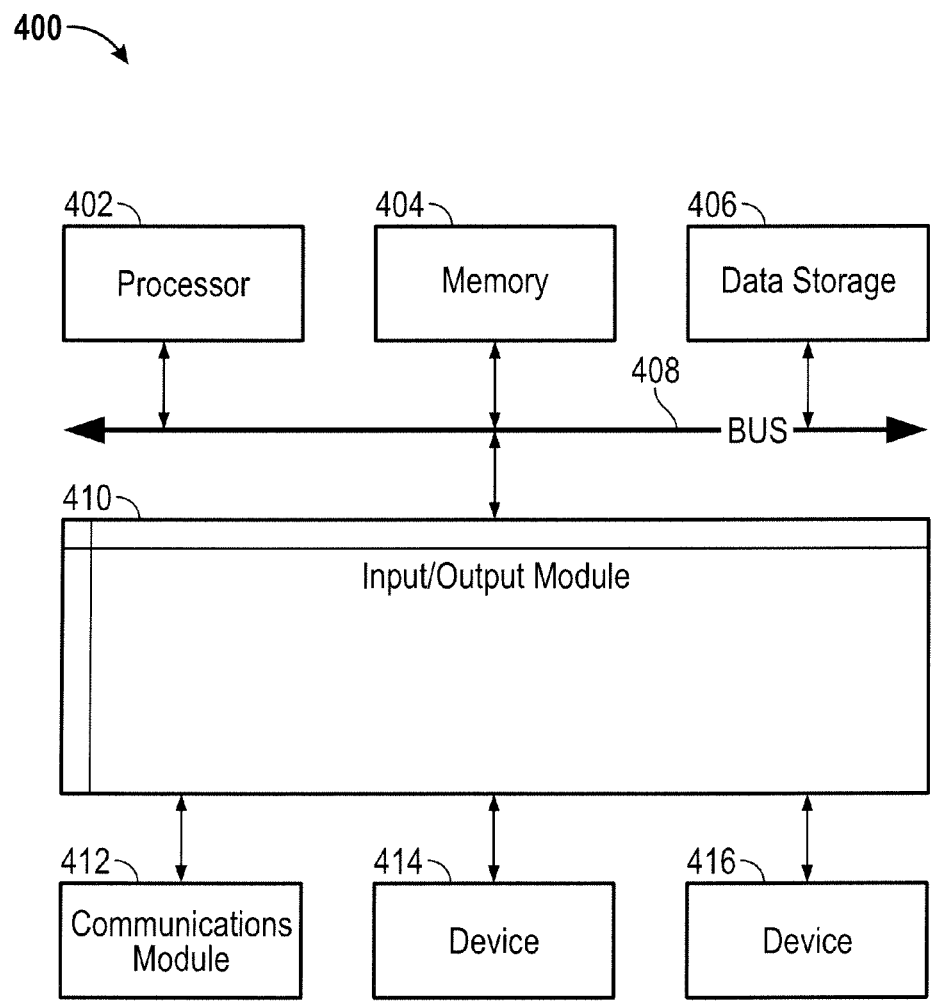
FIG. 4 is a block diagram illustrating an example computer system with which the control system, server, and medical device of FIG. 2 can be implemented.

FIG. 4 is a block diagram illustrating an example computer system 400 with which the control system 40, medical device 80, and server 130 of FIG. 2 can be implemented. In certain aspects, the computer system 400 may be implemented using hardware or a combination of software and hardware, either in a dedicated server, or integrated into another entity, or distributed across multiple entities.

Computer system 400 (e.g., control system 40, medical device 80, and server 130) includes a bus 408 or other communication mechanism for communicating information, and a processor 402 (e.g., processor 212, 154, and 136) coupled with bus 408 for processing information. By way of example, the computer system 400 may be implemented with one or more processors 402. Processor 402 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 400 can include, in addition to hardware, code that creates an execution environment for the computer program in question, e.g., code that constitutes processor firmware, a protocol stack, a database management system, an operating system, or a combination of one or more of them stored in an included memory 404 (e.g., memory 42, 152, and 132), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 408 for storing information and instructions to be executed by processor 402. The processor 402 and the memory 404 can be supplemented by, or incorporated in, special purpose logic circuitry.

The instructions may be stored in the memory 404 and implemented in one or more computer program products, i.e., one or more modules of computer program instructions encoded on a computer readable medium for execution by, or to control the operation of, the computer system 400, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 404 may also be used for storing temporary variable or other intermediate information during execution of instructions to be executed by processor 402.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 400 further includes a data storage device 406 such as a magnetic disk or optical disk, coupled to bus 408 for storing information and instructions. Computer system 400 may be coupled via input/output module 410 to various devices. The input/output module 410 can be any input/output module. Example input/output modules 410 include data ports such as USB ports. The input/output module 410 is configured to connect to a communications module 412. Example communications modules 412 (e.g., communications module 210, 156, and 138) include networking interface cards, such as Ethernet cards and modems. In certain aspects, the input/output module 410 is configured to connect to a plurality of devices, such as an input device 414 (e.g., input device 216) and/or an output device 416 (e.g., display device 214). Example input devices 414 include a keyboard and a pointing device, e.g., a mouse or a trackball, by which a user can provide input to the computer system 400. Other kinds of input devices 414 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 416 include display devices, such as a LED (light emitting diode), CRT (cathode ray tube), or LCD (liquid crystal display) screen, for displaying information to the user.

According to one aspect of the present disclosure, the control system 40, medical device 80, and server 130 can be implemented using a computer system 400 in response to processor 402 executing one or more sequences of one or more instructions contained in memory 404. Such instructions may be read into memory 404 from another machine-readable medium, such as data storage device 406. Execution of the sequences of instructions contained in main memory 404 causes processor 402 to perform the process steps described herein. One or more processors in a multi-processing arrangement may also be employed to execute the sequences of instructions contained in memory 404. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., network 30) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 400 can include clients and servers. A client and server are generally remote from each other and typically interact through a communication network. The relationship of client and server arises by virtue of computer programs running on the respective computers and having a client-server relationship to each other. Computer system 400 can be, for example, and without limitation, a desktop computer, laptop computer, or tablet computer. Computer system 400 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 402 for execution. Such a medium may take many forms, including, but not limited to, non-volatile media, volatile media, and transmission media. Non-volatile media include, for example, optical disks, magnetic disks, or flash memory, such as data storage device 406. Volatile media include dynamic memory, such as memory 404. Transmission media include coaxial cables, copper wire, and fiber optics, including the wires that comprise bus 408. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

These and other implementations are within the scope of the following claims.

What is claimed is:

1. A system, comprising:
a medical device that is configurable with operating limit parameters that limit operating parameters for providing medication to a patient; and
a limiting system comprising:
a memory comprising patient-specific information for the patient and a database comprising a plurality of sets of acceptable operating parameters for providing the medication to the patient using the medical device, the patient-specific information comprising patient demographic information and patient physiological information; and
a processor configured to:
compare the acceptable operating parameters with the patient-specific information before and during administration of the medication to the patient;
provide, to the medical device, a modification of the operating limit parameters based on the comparison of the patient-specific information with the acceptable operating parameters; and
provide a notification for display by the medical device indicating that the operating limit parameters for providing the medication to the patient have been modified based on the patient-specific information, the notification comprising information regarding the modified operating limit parameters,
wherein the medical device is configurable with the operating limit parameters for providing a mixture comprising a plurality of medications to the patient, wherein the acceptable operating parameters include acceptable operating parameters for providing the mixture to the patient using the medical device,
wherein the acceptable operating parameters comprise a plurality of rules indicating whether the patient-specific information comprises a value that is within or exceeds a threshold defined in accordance with a medical condition of the patient, and
wherein at least one of the rules indicates a maximum total amount of the medication to provide to the patient and a maximum total amount of the medication to provide to the patient over a period of time.

2. The system of claim 1, wherein the patient demographic information comprises at least one of an age of the patient, a gender of the patient, a genetic makeup of the patient, or an ethnicity of the patient.

3. The system of claim 2, wherein the patient physiological information includes at least one of a medication ordered for the patient, a time at which the medication is ordered for the patient, a treatment plan for the patient, a medication resistance of the patient, a weight of the patient, a height of the patient, or a body surface area of the patient.

4. The system of claim 3, wherein the processor is configured to compare the acceptable operating parameters with the patient-specific information by comparing a first weight of the patient provided to the medical device with a second weight of the patient provided to a different currently running medical device.

5. The system of claim 1, wherein the patient physiological information includes at least one of a medication ordered for the patient, a time at which the medication is ordered for the patient, a treatment plan for the patient, a medication resistance of the patient, a weight of the patient, a height of the patient, or a body surface area of the patient.

6. The system of claim 1, wherein the medical condition is determinable based on laboratory data of the patient comprising a blood coagulation measure, a vitamin level, a platelet count value, a thromboplastin time, a weight, or a serum level.

7. The system of claim 1, wherein the medical device comprises an infusion pump, and wherein the patient-specific information further comprises laboratory data for the patient.

8. The system of claim 1, wherein the operating limit parameters comprise at least one of a rate at which to provide the medication, an amount of the medication to provide, and a length of time to provide the medication.

9. The system of claim 1, wherein the processor is configured to provide the modification of the operating limit parameters based on the patient-specific information by defining at least one of a pair of a soft maximum value that can be exceeded and a hard maximum value that cannot be exceeded, or a soft minimum value that can be exceeded and a hard minimum value that cannot be exceeded for at least one operating limit parameter associated with delivery of the medication to the patient based on the patient-specific information.

10. The system of claim 1, wherein the patient-specific information further comprises laboratory data for the patient, the laboratory data comprising at least one of a blood coagulation measure, a vitamin level, a platelet count value, a thromboplastin time, or a serum level.

11. A system, comprising:
a medical device that is configurable with operating limit parameters that limit operating parameters for providing medication to a patient; and
a limiting system comprising:
a memory comprising patient-specific information for the patient and a database comprising a plurality of sets of acceptable operating parameters for providing the medication to the patient using the medical device; and
a processor configured to:
compare the acceptable operating parameters with the operating limit parameters and the patient-specific information before and during administration of the medication to the patient;
generate modified operating limit parameters for the medical device based on the comparison of the patient-specific information with the acceptable operating parameters;
provide a notification for display by the medical device indicating the modified operating limit parameters;
receive an input from a caregiver for the patient, the input including information indicating whether the modified operating limit parameters are accepted; and
provide the operating limit parameters or the modified operating limit parameters to the medical device responsive to the received input, wherein the medical device is configurable with the operating limit parameters for providing a mixture comprising a plurality of medications to the patient, wherein the acceptable operating parameters include acceptable operating parameters for providing the mixture to the patient using the medical device, wherein the acceptable operating parameters comprise a plurality of rules indicating whether the patient-specific information comprises a value that is within or exceeds a threshold defined in accordance with a medical condition of the patient, and wherein at least one of the rules indicates a maximum total amount of the medication to provide to the patient and a maximum total amount of the medication to provide to the patient over a period of time.

12. The system of claim 11, wherein the input from the caregiver comprises an acknowledgment from the caregiver that one or more of the operating parameters is a value that is outside a soft limit and that this value is nevertheless to remain in force.

13. The system of claim 11, wherein the input from the caregiver comprises an input to override the modified operating limit parameters, wherein the input from the caregiver comprises an indication of why the caregiver overrode the modified operating limit parameters, and wherein the processor is further configured to record when the caregiver overrides the modified operating limit parameters.

14. The system of claim 11, wherein the processor is further configured to receive configuration parameters for determining whether to provide the notification to the medical device based on at least one of an identity of a caregiver, a location of the medical device, or an institutional preference.

15. The system of claim 14, wherein the processor is further configured to receive the configuration parameters for determining whether to provide the notification to the medical device based on the identity of the caregiver and wherein the identity of the caregiver comprises a level of training and experience of the caregiver.

16. The system of claim 11, wherein the patient-specific information further comprises laboratory data for the patient, the laboratory data comprising at least one of a blood coagulation measure, a vitamin level, a platelet count value, a thromboplastin time, or a serum level.

17. A system for assisting a clinician in providing a patient therapy, the system comprising:
a medical device that is configurable with operating limit parameters that limit operating parameters for providing medication to a patient according to the patient therapy; and
a limiting system comprising:
a memory comprising patient-specific information for the patient and a database comprising a plurality of sets of acceptable operating parameters for providing the patient therapy using the medical device, the patient-specific information comprising laboratory data for the patient, the laboratory data comprising at least one of a blood coagulation measure, a vitamin level, a platelet count value, a thromboplastin time, or a serum level; and
a processor configured to:
compare the acceptable operating parameters with the laboratory data for the patient before and during administration of the medication to the patient;
and
provide a recommendation for altering the patient therapy based on the comparison of the acceptable operating parameters with the laboratory data for the patient
wherein the medical device is configurable with the operating limit parameters for providing a mixture comprising a plurality of medications to the patient, wherein the acceptable operating parameters include acceptable operating parameters for providing the mixture to the patient using the medical device,
wherein the acceptable operating parameters comprise a plurality of rules indicating whether the patient-specific information comprises a value that is within or exceeds a threshold defined in accordance with a medical condition of the patient, and
wherein at least one of the rules indicates a maximum total amount of the medication to provide to the patient, and a maximum total amount of the medication to provide to the patient over a period of time.

18. The system of claim 17, wherein the processor is configured to provide the recommendation for altering the patient therapy by:
generating modified operating limit parameters for the medical device; and
providing a notification to the clinician of the modified operating limit parameters.

19. The system of claim 17, wherein the processor is further configured to receive an input from the clinician, the input including information indicating whether the altered patient therapy is accepted.

20. The system of claim 17, wherein the medical device comprises an infusion pump.

21. The system of claim 17, wherein the patient-specific information further comprises at least one of a medication ordered for the patient, a time at which the medication is ordered for the patient, a treatment plan for the patient, a medication resistance of the patient, a weight of the patient, a height of the patient, a body surface area of the patient, an age of the patient, a gender of the patient, a genetic makeup of the patient, or an ethnicity of the patient, and wherein comparing the acceptable operating parameters with laboratory data comprises comparing a first weight of the patient provided to the medical device with a second weight of the patient provided to another medical device.

* * * * *